(12) United States Patent
Adler et al.

(10) Patent No.: US 9,981,992 B2
(45) Date of Patent: May 29, 2018

(54) COMPOSITIONS AND METHODS FOR REDUCTION OF KETONES, ALDEHYDES AND IMINIUMS, AND PRODUCTS PRODUCED THEREBY

(71) Applicants: Marc J. Adler, Vaughan (CA); Thomas M. Gilbert, St. Charles, IL (US); Sami E. Varjosaari, DeKalb, IL (US); Vladislav Skrypai, DeKalb, IL (US)

(72) Inventors: Marc J. Adler, Vaughan (CA); Thomas M. Gilbert, St. Charles, IL (US); Sami E. Varjosaari, DeKalb, IL (US); Vladislav Skrypai, DeKalb, IL (US)

(73) Assignee: The Board of Trustees of Northern Illinois University, DeKalb, IL (US)

( * ) Notice: Subject to any disclaimer, the term of this patent is extended or adjusted under 35 U.S.C. 154(b) by 0 days. days.

(21) Appl. No.: 15/186,306

(22) Filed: Jun. 17, 2016

(65) Prior Publication Data
US 2017/0362151 A1 Dec. 21, 2017

Related U.S. Application Data

(60) Provisional application No. 62/351,178, filed on Jun. 16, 2016.

(51) Int. Cl.
| | |
|---|---|
| *C07F 7/02* | (2006.01) |
| *C07F 7/04* | (2006.01) |
| *C07C 41/26* | (2006.01) |
| *C07C 253/30* | (2006.01) |
| *C07C 201/12* | (2006.01) |
| *C07C 29/143* | (2006.01) |
| *C07C 209/00* | (2006.01) |
| *C07C 29/14* | (2006.01) |
| *C07D 307/00* | (2006.01) |

(52) U.S. Cl.
CPC .............. *C07F 7/045* (2013.01); *C07C 29/14* (2013.01); *C07C 29/143* (2013.01); *C07C 41/26* (2013.01); *C07C 201/12* (2013.01); *C07C 209/00* (2013.01); *C07C 253/30* (2013.01); *C07D 307/00* (2013.01); *C07C 2101/14* (2013.01); *C07C 2601/14* (2017.05); *C07C 2602/10* (2017.05); *C07C 2603/24* (2017.05); *C07C 2603/30* (2017.05)

(58) Field of Classification Search
CPC ..... C07C 37/002; C07C 29/143; C07C 41/26; C07C 201/12; C07C 209/00; C07C 253/30; C07F 7/045
USPC ........................................................ 556/408
See application file for complete search history.

(56) References Cited

PUBLICATIONS

Attar-Bashi et al. Journal of Organometallic Chemistry, 117 (1976) C87-C89.*

Fujita et al., J. Org. Chem. 1988, 53, 5405-5415.*

Schlesinger, H.I. et al., "Sodium borohydride, its hydrolysis and its use as a reducing agent and in the generation of hydrogen", Journal of the American Chemical Society, vol. 75, pp. 215-219, (1953).

Schlesinger, H.I. et al., "New developments in the chemistry of diborane and the borohydrides. I. General summary", Journal of the American Chemical Society, vol. 75, pp. 186-190, (1953).

Jia, Z. et al., "Highly efficient reduction of aldehydes with silanes in water catalyzed by silver", Synlett, vol. 24, pp. 2049-2056, (2013).

Fujita, M. et al., "Fluoride ion catalyzed reduction of aldehydes and ketones with hydrosilanes. Synthetic and mechanistic aspects and an application to the threo-directed reduction of α-substituted alkanones", Journal of Organic Chemistry, vol. 53, No. 23, pp. 5405-5415, (1988).

Doyle, M.P. et al., "Silane reductions in acidic media. III. reductions of aldehydes and ketones to alcohols and alcohol derivatives. general syntheses of alcohols, symmetrical ethers, carboxylate esters, and acetamides", Journal of Organic Chemistry, vol. 39, No. 18, pp. 2740-2747, (1974).

Fujita, M. et al., "Highly diastereocontrolled reduction of ketones by means of hydrosilanes, practical synthesis of optically active 1,2-diols and 2-amino alcohols of threo or erythro configuration", Journal of the American Chemical Society, vol. 106, pp. 4629-4630, (1984).

Gan, L. et al., "Hydrosilylation of ketones catalyzed by $C_2$-symmetric proline-derived complexes", Canadian Journal of Chemstry, vol. 84, pp. 1416-1425, (2006).

Ojima, I. et al., "Stereoselective reduction of ketones with hydrosilane-rhodium(I) complex combinations", Bulletin of the Chemical Society of Japan, vol. 45, No. 12, p. 3722, (1972).

Mimoun, H. et al., "Enantioselective reduction of ketones by polymethylhydrosiloxane in the presence of chiral zinc catalysts", Journal of the American Chemical Society, vol. 121, No. 26, pp. 6158-6166, (1999).

Bhattacharyya, S., "Titanium(IV) chloride-triethylsilane: An efficient, mild system for the reduction of acylferrocenes to alkylferrocenes", Journal of Organic Chemistry, vol. 63, No. 20, pp. 7101-7102, (1998).

Mizuta, T. et al., "Catalytic reductive alkylation of secondary amine with aldehyde and silane by an iridium compound", Journal of Organic Chemistry, vol. 70, No. 6, pp. 2195-2199, (2005).

Doyle, M.P. et al., "Silane reductions in acidic media. VI. the mechanism of organosilane reductions of carbonyl compounds. transition state geometries of hydride transfer reactions", Journal of Organic Chemistry, vol. 40, No. 26, pp. 3835-3838, (1975).

Gevorgyan, V. et al., "A direct reduction of aliphatic aldehyde, acyl chloride, ester, and carboxylic functions into a methyl group", Journal of Organic Chemistry, vol. 66, No. 5, pp. 1672-1675, (2001).

Gandhamsetty, N. et al., "Boron-catalyzed silylative reduction of nitriles in accessing primary amines and imines", Journal of Organic Chemistry, vol. 80, pp. 7281-7287, (2015).

(Continued)

*Primary Examiner* — Rosalynd Keys
*Assistant Examiner* — Kofi Adzamli
(74) *Attorney, Agent, or Firm* — Evan Law Group LLC

(57) ABSTRACT

A method of producing an alcohol, comprises reducing an aldehyde or a ketone with a hydridosilatrane. The reducing is carried out with an activator.

25 Claims, 8 Drawing Sheets

(56) References Cited

PUBLICATIONS

Rendler, S. et al., "Conclusive evidence for an $S_N2$—Si mechanism in the $B(C_6F_5)_3$-catalyzed hydrosilylation of carbonyl compounds: Implications for the related hydrogenation", Angewandte Chemie International Edition, vol. 47, pp. 5997-6000, (2008).

Fedorov, A. et al., "Lewis-base silane activation: from reductive cleavage of aryl ethers to selective ortho-silylation", Chemical Science, vol. 4, pp. 1640-1645, (2013).

Rubio, M. et al., "Rhodium-catalyzed, efficient deutero- and tritiosilylation of carbonyl compounds from hydrosilanes and deuterium or tritium", Organic Letters, vol. 13, No. 19, pp. 5236-5239, (2011).

Matsubara, K. et al., "A triruthenium carbonyl cluster bearing a bridging acenaphthylene ligand: An efficient catalyst for reduction of esters, carboxylic acids, and amides by trialkylsilanes", Journal of Organic Chemistry, vol. 67, No. 14, pp. 4985-4988, (2002).

Denmark, S.E. et al., "Palladium-catalyzed cross-coupling reactions of silanolates: A paradigm shift in silicon-based cross-coupling reactions", Chemistry A European Journal, vol. 12, pp. 4954-4963, (2006).

Metsanen, T.T. et al., "Temperature-dependent chemoselective hydrosilylation of carbon dioxide to formaldehyde or methanol oxidation state", Organometallics, vol. 34, pp. 543-546, (2015).

Díez-González, S. et al., "Cationic copper(I) complexes as efficient precatalysts for the hydrosilylation of carbonyl compounds", Organometallics, vol. 25, pp. 2355-2358, (2006).

Zhou, H. et al., "Synthesis and reactivity of a hydrido CNC pincer cobalt(III) complex and its application in hydrosilylation of aldehydes and ketones", Organometallics, vol. 34, pp. 1479-1486, (2015).

Reuther, V.H., "Zur kinetic der verseifung von triathoxysilan", Zeitschrift fur anorganische and allgemeine Chemie, vol. 272, issue 1-4, pp. 122-125, (1953).

Roth, M.J. et al., "Hydrosilane cleavage reactions accelerated by tartaric acid and dimethyl sulphoxide", Journal of Organometallic Chemistry, vol. 521, pp. 65-74, (1996).

Wells, A.S., "On the perils of unexpected silane generation", Organic Process Research & Development, vol. 14, p. 484, (2010).

Zhao, M. et al., "Cesium carbonate catalyzed chemoselective hydrosilylation of aldehydes and ketones under solvent-free conditions", Chemistry A European Journal, vol. 20, pp. 9259-9262, (2014).

Junge, K. et al., "Copper-catalyzed enantioselective hydrosilylation of ketones by using monodentate binaphthophosphepine ligands", Chemistry A European Journal, vol. 16, pp. 68-73, (2010).

Revunova, K. et al., "Base-catalyzed hydrosilylation of ketones and esters and insight into the mechanism", Chemistry A European Journal, vol. 20, pp. 839-845, (2014).

Attar-Bashi, M.T. et al., "Silatrane as a reducing agent", Journal of Organometallic Chemistry, vol. 117, pp. C87-C89, (1976).

Puri, J.K. et al., "Silatranes: a review on their synthesis, structure, reactivity and applications", Chemical Society Reviews, vol. 40, pp. 1791-1840, (2011).

Frye, C.L. et al., "Pentacoordinate silicon compounds. V. novel silatrane chemistry", Journal of the American Chemical Society, vol. 93, No. 25, pp. 6805-6811, (1971).

Voronkov, M.G. et al., "Silatranes", Journal of Organometallic Chemistry, vol. 233, pp. 1-147, (1982).

Verkade, J.G. et al., "Atranes: New examples with unexpected properties", Accounts of Chemical Research, vol. 26, No. 9, pp. 483-489, (1993).

Kira, M. et al., "Reduction of carbonyl compounds with pentacoordinate hydridosilicates", Journal of Organic Chemistry, vol. 52, pp. 948-949, (1987).

Brellere, C. et al., "Pentacoordinated silicon hydrides: Very high affinity of the Si—H bond for the equatorial position", Organometallics, vol. 5, pp. 388-390, (1986).

Deneux, M. et al., "Reactions des trialkylsilanes catalysees par l'ion fluorure", Bull. Soc. Chim. Fr, pp. 2638-2642, (1973).

Boyer, J. et al., "Enhancement of Si—H bond reactivity in pentacoordinated structures", Journal of Organometallic Chemistry, vol. 311, pp. C39-C43, (1986).

Pietruszka, J., "Product subclass 4: Silyl hydrides", Science of Synthesis, vol. 4, pp. 159-185, (2002).

Chuit, C. et al., "Structure and reactivity of hypercoordinate silicon species", Chemistry of Hypervalent Compounds, Wiley-VCH, Weinheim, Germany, pp. 81-146, (1999).

Aizpurua, J.M. et al., "Reduction of carbonyl compounds promoted by silicon hydrides under the influence of trimethylsilyl-based reagents", Canadian Journal of Chemistry, vol. 64, pp. 2342-2347, (1986).

Aizpurua, J.M. et al., "Synthesis of benzyl halides from aldehydes promoted by halosilanes and 1,1,3,3-tetramethyldisiloxane (TMDS)", Tetrahedron Letters, vol. 25, No. 10, pp. 1103-1104, (1984).

West, C.T. et al., "Silane reductions in acidic media. II. Reductions of aryl aldehydes and ketones by trialkylsilanes in trifluoroacetic acid. A selective method for converting the carbonyl group to methylene", Journal of Organic Chemistry, vol. 38, No. 15, pp. 2675-2681, (1973).

Geissman, T.A., "The Cannizzaro Reaction", Organic Reactions, vol. II, chapter 3, pp. 94-113, (1946).

Karlov, S.S. et al., "Synthesis and characterization of metallatranes with phenyl substituents in atrane cage", Inorganica Chimica Acta, vol. 360, pp. 563-578, (2007).

Black, C.A. et al., "Stereoselective and improved syntheses and anticancer testing of 3'-O-silatranylthymidines", Bioorganic & Medicinal Chemistry Letters, vol. 12, pp. 3521-3523, (2002).

Lukevics, E. et al., "A new reaction of 1-hydrosilatrane", Main Group Metal Chemistry, vol. 23, No. 12, pp. 761-764, (2000).

Pestunovich, V.A. et al., "Silatranation reaction. reaction of 1-iodosilatrane with oxygen-containing compounds", Dokl. Akad. Nauk, vol. 263, pp. 904-906, (1982).

Magano, J. et al., "Large-scale carbonyl reductions in the pharmaceutical industry", Organic Process Research & Development, vol. 16, pp. 1156-1184, (2012).

Abdel-Magid, A.F., "Reduction of C=N To CH—NH by metal hydrides", Comprehensive Organic Synthesis II, vol. 8, pp. 85-150, (2014).

Hudlicky, M., "Reductions in Organic Chemistry", Ellis Horwood Limited, pp. 1-267, (1984).

Abdel-Magid, A.F., "Reduction of C=O to CHOH by Metal Hydrides", Comprehensive Organic Synthesis II, vol. 8, pp. 1-84, (2014).

Cho, B.T., "Recent development and improvement for boron hydride-based catalytic asymmetric reduction of unsymmetrical ketones", Chemical Society Reviews, vol. 38, pp. 443-452, (2009).

Wang, D., et al., "Chiral silicon compounds. Asymmetric reduction of ketones", Tetrahedron Letters, vol. 24, No. 15, pp. 1573-1576, (1983).

Lipshutz, B.H. et al., "Asymmetric hydrosilylation of aryl ketones catalyzed by copper hydride complexed by nonracemic biphenyl bis-phosphine ligands", Journal of the American Chemical Society, vol. 125, pp. 8779-8789, (2003).

Liu, S. et al., "Highly efficient and convenient asymmetric hydrosilylation of ketones catalyzed with zinc Schiff base complexes", Tetrahedron, vol. 68, No. 1371-1375, (2012).

Hog, D.T. et al., "$B(C_6F_5)_3$-catalyzed reduction of ketones and imines using silicon-stereogenic silanes: Stereoinduction by single-point binding", European Journal of Organic Chemistry, vol. 136, pp. 5047-5056, (2009).

Chen, J. et al., "Synthesis and lewis acid properties of a ferrocene-based planar-chiral borenium cation", Chemical Communications, vol. 49, No. 43, pp. 4893-4895, (2013).

Metsänen, T.T., "Insight into the mechanism of carbonyl hydrosilylation catalyzed by brookhart's cationic iridium(III) pincer complex", Journal of the American Chemical Society, vol. 136, pp. 6912-6915, (2014).

Boyer, J. et al., "Reduction selective de composes carbonyls par catalyse heterogene a la surface des sels", Tetrahedron, vol. 37, pp. 2165-2171, (1981). English Language Abstract.

(56) References Cited

OTHER PUBLICATIONS

Corriu, R.J.P. et al., "Activation of silicon-hydrogen, silicon-oxygen, silicon-nitrogen bonds in heterogeneous phase", Tetrahedron, vol. 39, No. 6, pp. 999-1009, (1983).
Kobayashi, Y. et al., "Reduction of carbonyl compounds by using polymethylhydro-siloxane: Reactivity and Selectivity", Tetrahedron, vol. 53, No. 5, pp. 1627-1634, (1997).
Drew, M.D. et al., "The asymmetric reduction of ketones using chiral ammonium fluoride salts and silanes", Tetrahedron Letters, vol. 38, No. 33, pp. 5857-5860, (1997).
Hosomi, A. et al., "Pentaco-ordinate silicon compounds in synthesis: Chemo- and stereo-selective reduction of carbonyl compounds using trialkoxy-substituted silanes and alkali metal alkoxides", Journal of the American Chemical Society, Chemical Communications, vol. 18, pp. 1411-1412, (1986).
Kohra, S. et al., "Pentaco-ordinate organosilicon compounds in synthesis: Asymmetric reduction of carbonyl compounds with hydrosilanes catalyzed by chiral bases", Tetrahedron Letters, vol. 29, No. 1, pp. 89-92, (1988).
Schiffers, R. et al., "Asymmetric catalytic reduction of ketones with hypervalent trialkoxysilanes", Synlett, pp. 1175-1178, (1997).
LaRonde, F.J. et al., "Stereoselective reduction of ketones using extracoordinate silicon: $C_2$-symmetric ligands", Inorganica Chimica Acta, vol. 296, pp. 208-221, (1999).
Corriu, R.J.P., "Hypervalent species of silicon: structure and reactivity", Journal of Organometallic Chemistry, vol. 400, pp. 81-106, (1990).
Rendler, S. et al., "Hypervalent silicon as a reactive site in selective bond-forming processes", Synthesis, vol. 11, pp. 1727-1747, (2005).
Denmark, S.E. et al., "Lewis base catalysis in organic synthesis", Angewandte Chemie International Edition, vol. 47, pp. 1560-1638, (2008).
Korlyukov, A.A., "Coordination compounds of tetravalent silicon, germanium and tin: the structure, chemical bonding and intermolecular interactions in them", Russian Chemical Reviews, vol. 84, No. 4, pp. 422-440, (2015).
Marin-Luna, M. et al., "Theoretical study of the geometrical, energetic and NMR properties of atranes", Journal of Organometallic Chemistry, vol. 794, pp. 206-215, (2015).
Frye, C.L. et al., "Triptych-siloxazolidines: Pentacoordinate bridgehead silanes resulting from trasannular interaction of nitrogen and silicon", Journal of the American Chemical Society, vol. 83, pp. 996-997, (1961).
Singh, G. et al., "Synthesis and characterization of modified Schiff base silatranes (MSBS) via Click Silylation", Journal of Molecular Structure, vol. 1079, pp. 173-181, (2015).
Skrypai, V. et al., "Silatrane as a practical and selective reagent for the reduction of aryl aldehydes to benzylic alcohols", European Journal of Organic Chemistry, vol. 12, pp. 2207-2211, (2016).
Bahia, P.S. et al., "Al-isopropoxydiisobutylalane: A Study of the effect of solvent on the rate and stereoselectivity of cyclic ketone reduction", The Journal of Organic Chemistry, vol. 69, No. 26, pp. 9289-9291, (2004).
Sok, S. et al., "A dash of protons: A theoretical study on the hydrolysis mechanism of 1-substituted silatranes and their protonated analogs", Computational and Theoretical Chemistry, vol. 987, pp. 2-15, (2012).
Haut, S.A., "A convenient preparation of pure menthol and menthone isomers", Journal of Agricultural and Food Chemistry, vol. 33, No. 2, pp. 278-280, (1985).
Hedin-Dahlström, J. et al., "Stereoselective reduction of menthone by molecularly imprinted polymers", Tetrahedron: Asymmetry, vol. 15, pp. 2431-2436, (2004).
Dieskau, A.P. et al., "$Bu_4N[Fe(CO)_3(NO)]$-catalyzed hydrosilylation of aldehydes and ketones", European Journal of Organic Chemistry, pp. 5291-5296, (2011).
Fujiwara, Y. et al., "Facile hydrogenation of ketones catalyzed by platinum on carbon under ordinary pressures and temperatures", ChemCatChem, vol. 3, pp. 1624-1628, (2011).
Mahdi, T. et al., "Enabling catalytic ketone hydrogenation by frustrated lewis pairs", Journal of the American Chemical Society, vol. 136, pp. 15809-15812, (2014).
Hegedus, L.S. et al., "Synthetic applications of transition metal hydrides", Transition Metals in the Synthesis of Complex Organic Molecules, Chapter 3, pp. 36-66, (2010).
Mun, S-d. et al., "Titanatranes containing tetradentate ligands with controlled steric hindrance", Journal of Organometallic Chemistry, vol. 692, pp. 3519-3525, (2007).
Chang, I-S. et al., "Fluorinated alkoxides. Part XI. Studies on highly fluorinated amino-alcohols and their metal derivatives", Canadian Journal of Chemistry, vol. 55, 99. 2465-2472, (1977).
Shanklin, J. R. et al., "Conversion of Ketones to Epoxides via β-Hydroxy Sulfides", Journal of the American Chemical Society, vol. 95, pp. 3429-3431, (1973).
Jones, T.K. et al., "An asymmetric synthesis of MK-0417. Observations on oxazaborolidine-catalyzed reductions", Journal of Organic Chemistry, vol. 56, pp. 763-769, (1991).
Corey, E.J. et al., "Reduction of carbonyl compounds with chiral oxazaborolidine catalysts: A new paradigm for enantioselective catalysis and a powerful new synthetic method", Angewandte Chemie International Edition, vol. 37, pp. 1986-2012, (1998).
Duran, J. et al., "Synthesis and characterization of a new chiral phosphinothiol ligand derived from (--)-menthone and its palladium(II) and platinum(II) complexes", Organometallics, vol. 22, pp. 3432-3438, (2003).
Wagner, G. et al., "Synthesis and structure of chiral silatranes derived from terpenes", Zeitschrift fur Naturforschung B, vol. 56, No. 1, pp. 25-38, (2001).
Varjosaari, S.E. et al., "1-Hydrosilatrane: a locomotive for efficient ketone reductions", European Journal of Organic Chemistry, vol. 2017, issue 2, pp. 229-232, (2017).
Denmark, S.E. et al., "Catalytic enantioselective addition of allylic organometallic reagents to aldehydes and ketones", Chemical Reviews, vol. 103, No. 8, pp. 2763-2793, (2003).
Leighton, J.L. et al., "Powerful and versatile silicon lewis acids for asymmetric chemical synthesis", Aldrichimica Acta, vol. 43, No. 1, pp. 3-12, (2010).
Yoshimura, M. et al., "Recent topics in catalytic asymmetric hydrogenation of ketones", Tetrahedron Letters, vol. 55, pp. 3635-3640, (2014).
Varjosaari, S.E. et al., "A fork in the railroad: Ketone reductions with 1-hydrosilatrane", 47th Si Symposium 2016, 2 pages, (2016).
Skrypai, V. et al., "Reductive rail yard: Versatility of 1-Hydrosilatrane", 47th Si Symposium 2016, 2 pages, (2016).
Varjosaari, S.E. et al., "Simple metal-free direct reductive amination using hydrosilatrane to form secondary and tertiary amines", Advanced Synthesis & Catalysis, vol. 359, pp. 1872-1878, (2017).
Skrypai, V. et al., "Reductive rail yard: Versatility of 1-Hydrosilatrane", 47th Si Symposium 2016, 1 page, poster abstract, Jun. 19-22, 2016.
Varjosaari, S.E. et al., "A fork in the railroad: Ketone reductions with 1-hydrosilatrane", 47th Si Symposium 2016, 1 page, poster abstract, Jun. 19-22, 2016.
Si Symposium, "Program and book of abstracts 47th silicon symposium Jun. 19-22, 2016", 47th Si Symposium 2016, pp. 1-6, 73, 78, (2016).
Varjosaari, S.E. et al., "1-Hydrosilatrane: A locomotive for efficient ketone reductions", European Journal of Organic Chemistry, vol. 2017, issue 2, supporting information, pp. 1-54, (2016).
Pestunovich, V. et al., "Silatranes and their tricyclic analogs", The Chemistry of Organic Silicon Compounds, vol. 2, parts 1-3, pp. 1447-1537, (2003).
Zelchan, G.I. et al., "1-Hydrosilatranes", Chemistry of Heterocyclic Compounds, vol. 3, No. 2, pp. 296-298, (1967).

\* cited by examiner

COMPOSITIONS AND METHODS FOR REDUCTION OF KETONES, ALDEHYDES AND IMINIUMS, AND PRODUCTS PRODUCED THEREBY

BACKGROUND

The reduction of carbonyl groups is one of the most significant chemical transformations in chemistry, giving access to a plethora of products from simple starting materials.[20] The development of chiral reducing agents has given access to asymmetric products[20a], including the crucially important optically pure secondary alcohols, from prochiral ketones.[21] Commonly available reducing agents have some drawbacks. Aluminohydrides and trialkylborohydrides decompose rapidly in protic solvents, such as alcohols. $NaBH_4$ reacts only slowly with protic solvents, but dissolves poorly in nonpolar solvents. More powerful reducing agents, such as $LiAlH_4$, are not particularly selective or tolerant of functional groups. Transition metal-based reductants share these drawbacks: many are too expensive for large-scale syntheses, and those useful for asymmetric synthesis are difficult to prepare and handle. Reducing organic carbonyls stereoselectively/stereospecifically to give chiral alcohols is a regularly sought goal, using expensive transition metal based reductants,[43] or the CBS catalyst using boron-based reagents,[49] although one intriguing case employing trialkoxysilanes and Lewis bases has appeared.[44]

Hydrosilanes are also versatile reducing agents for a variety of organic functionalities[2] including aldehydes[3] and ketones.[4] Similar to the pervasive borohydrides, the Si—H bond is polarized towards the hydrogen allowing silanes to serve as mild sources of hydride. Silanes are readily and cheaply available, as silicon is the second most abundant element in the earth's crust. Despite this significant advantage with respect both to environmental friendliness and cost as compared to borohydrides, the synthetic community has not yet developed a widely applied, operationally simple, mild, cheap, bench top method for the reduction of carbonyl groups using silanes.

The main reason for this state of affairs is that silane reactivity is difficult to tune. While alkylsilanes (such as triethylsilane) are generally easy to handle,[5] they require forceful activation in the form of a Brønsted acid,[6] Lewis acid,[7] Lewis base,[8] or transition metal[9] in the reaction mixture; the method by which these additives catalyze the reaction varies, but their presence is vital to enhance the hydridic nature of the hydrosilane. Silanes bearing more electronegative substituents (such as alkoxy or halide) or multiple hydrides are more reactive, allowing for the development of many excellent methods, yet simultaneously making them difficult—or at least inconvenient—to handle.[10] For example, Nikinov and co-workers described a useful and economical method to reduce carbonyls to alcohols using the readily available polymethylhydrosiloxane (PMHS) with catalytic hydroxide in a sealed vial within a glovebox; this method necessitates the use of a carefully sealed reaction vessel and moisture-free techniques as the active reducing agent is the volatile and highly reactive $SiR_4$.[11] Silane reduction of aldehydes are frequently accompanied by the formation of symmetric ethers or, particularly in the case of aryl aldehydes, deoxygenated products.[16] While methods have been developed to control the product ratios in known systems, application to novel molecules requires optimization on a case-by-case basis.

Silatranes are characterized as caged structures, in which the nitrogen atom donates its lone pair of electrons to form a pentacoordinate silicon.[29] Since their discovery in the 1960s,[30] they have been extensively studied for myriad uses.[31] 1-Hydrosilatrane (1) has been less studied than other silatranes due to its anomalous physical properties and its challenging synthesis. However, it is an ideal candidate as a reducing agent due to its pentacoordinate silicon atom and its relatively high stability with respect to other silanes.[32]

In 1976, Eaborn and co-workers reported the use of 1-hydrosilatrane (1) as a reducing reagent.[12] These reactions provided poor yield and required forcing conditions. In more detail, the reductions of aldehydes and ketones carried out by Eaborn and co-workers were all carried out at a temperature of 140-180° C., for a time of 22-72 hours. The solvents were xylene, benzene and diethylene glycol diethyl ether. The reduction carried out in diethylene glycol diethyl ether at a temperature of 180° C. with an 8-fold excess of 1-hydrosilatrane, resulted in a yield of 70%; the other two reductions of an aldehyde and a ketone produced yields of 32 and 46%, respectively. Since Eaborn and co-workers disclosed this finding, the enhanced reactivity of hydrosilatrane has been discussed several times in the literature.[2, 15]

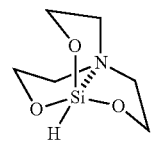

1

In silatranes the lone pair of the nitrogen—fixed directly opposed to the axial substituent—has been shown to donate into the σ* orbital of the axial substituent.[13] It is presumably by this mechanism that the hydrosilatrane is activated, with the intramolecular coordination of the nitrogen playing the role of a Lewis base additive. Similar types of intramolecular activation of hydrosilanes have been demonstrated.[14] Because of their structural rigidity, silatranes exhibit remarkable stability when compared to both other pentavalent silanes and other silyl orthoesters.

SUMMARY

In a first aspect, the present invention is a method of producing an alcohol, comprising reducing an aldehyde or a ketone with a hydridosilatrane. The reducing is carried out with an activator.

In a second aspect, the present invention is a method of producing an alcohol, comprising reducing an aldehyde or a ketone with a hydridosilatrane in water.

In a third aspect, the present invention is a method of producing a pharmaceutical compound, comprising forming an alcohol by the method of the prior aspects, and forming the pharmaceutical compound from the alcohol.

In a fourth aspect, the present invention is a method of producing an amine by reductive amination, comprising reacting an aldehyde or a ketone, with an amine and a hydridosilatrane.

In a fifth aspect, the present invention is a method of producing an amine, comprising reducing an iminium with a hydridosilatrane.

In a sixth aspect, the present invention is a kit, comprising (1) a hydridosilatrane in a first container, (2) an activator in a second container, and (3) a package. The first container and the second container are in the package.

In a seventh aspect, the present invention is a hydridosilatrane. The hydridosilatrane is chiral and comprises a bulky group comprising 4 to 12 carbon atoms.

Definitions

Hydridosilatranes are compounds of formula (I) or formula (II), wherein each $R^1$-$R^{12}$ are independently selected from H, OH, $OR^{13}$, $NR^{14}R^{15}$, aryl, alkyl and alkenyl, and $R^{13}$, $R^{14}$ and $R^{15}$ are each independently selected from H, OH, aryl, alkyl and alkenyl; and pairs of R groups which are bonded to the same carbon atom, together with the carbon atom, form a carbonyl group (C=O). Examples of hydridosilatranes are shown in FIG. 8.

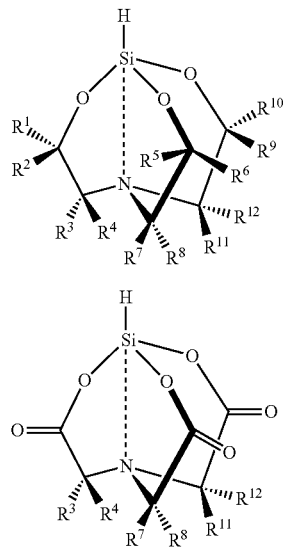

A prochiral ketone means a ketone where the groups bonded to the carbon of the carbonyl group (C=O) are different.

A prochiral iminium means an iminium where the groups bonded to the carbon of the iminium group (C=N) are different.

An aryl carbonyl or aromatic carbonyl is a compound which contains a carbonyl group directly attached to an aromatic ring. An alkyl carbonyl is a compound which contains a carbonyl directly attached to an alkyl group. Such compounds include ketones and aldehydes.

An aromatic ring or aryl group refers to any aromatic carbocyclic or heteroaromatic group, preferably of 3 to 10 carbon atoms. The aromatic ring or aryl group can be monocyclic (for example, phenyl (or Ph)) or polycyclic (for example, naphthyl) and can be unsubstituted or substituted. Preferred aryl groups include phenyl, naphthyl, furyl, thienyl, pyridyl, indolyl, quinolinyl or isoquinolinyl.

Alkyl (or alkyl- or alk-) refers to a substituted or unsubstituted, straight, branched or cyclic hydrocarbon chain, preferably containing from 1 to 20 carbon atoms. More preferred alkyl groups are alkyl groups containing from 2 to 10 carbon atoms. Preferred cycloalkyls have from 3 to 10, preferably 3 to 6, carbon atoms in their ring structure. Suitable examples of unsubstituted alkyl groups include methyl, ethyl, propyl, isopropyl, cyclopropyl, butyl, isobutyl, tert-butyl, sec-butyl, cyclobutyl, pentyl, cyclopentyl, hexyl, and cyclohexyl. Alkylaryl and alkylheterocyclic groups are alkyl groups covalently bonded to an aryl or heterocyclic group, respectively.

Alkenyl refers to a substituted or unsubstituted, straight, branched or cyclic, unsaturated hydrocarbon that contains at least one double bond, and preferably 2 to 20, more preferably 2 to 10, carbon atoms. Exemplary unsubstituted alkenyl groups include ethenyl (or vinyl)(—CH CH=CH$_2$), 1-propenyl, 2-propenyl (or allyl)(—CH$_2$—CH=CH$_2$), 1,3-butadienyl (—CH=CHCH=CH$_2$), 1-butenyl (—CH=CHCH$_2$CH$_3$), hexenyl, pentenyl, 1,3,5-hexatrienyl, and the like. Preferred cycloalkenyl groups contain 5 to 8 carbon atoms and at least one double bond. Examples of cycloalkenyl groups include cyclohexadienyl, cyclohexenyl, cyclopentenyl, cycloheptenyl, cyclooctenyl, cyclohexadienyl, cyclopentadienyl, and cyclooctatrienyl.

Substituted means that the moiety contains at least one, preferably 1 to 3, substituent(s). Suitable substituents include hydroxyl (—OH), amino (—NH$_2$), oxy (—O—), carbonyl (—CO—), thiol, alkyl, alkenyl, alkynyl, alkoxy, halo, nitrile, nitro, aryl and heterocyclic groups. These substituents can optionally be further substituted with 1 to 3 substituents. Examples of substituted substituents include carboxamide, alkylmercapto, alkylsulphonyl, alkylamino, dialkylamino, carboxylate, alkoxycarbonyl, alkylaryl, aralkyl, and alkylheterocyclic. Two or more substituents may be attached together, to form rings or clusters. Furthermore, a single substituent may be a substituent to multiple compounds, for example two hydridosilatranes may be attached to a single substituent to for a dimer, or many hydridosilatranes could be attached to a single polymer change. Also included as substituents are solid supports, surfaces and polymers, for example polystyrene beads and particles, and glass surfaces.

A bulky group is a substituent having 3 or more carbon atoms, such as 4 to 12 carbon atoms, preferably branched.

A pharmaceutical compound is an organic compound which has a biological effect and may be used to treat or prevent a disease or condition. Examples include dorzolamide (TRUSOPT®; (4S,6S)-4-(ethylamino)-6-methyl-7,7-dioxo-5,6-dihydro-4H-thieno[2,3-b]thiopyran-2-sulfonamide; administered as dorzolamide hydrochloride)[48], rosuvastatin (CRESTOR®; (3R,5S,6E)-7-[4-(4-fluorophenyl)-2-(N-methylmethanesulfonamido)-6-(propan-2-yl)pyrimidin-5-yl]-3,5-dihydroxyhept-6-enoic acid; administered as rosuvastatin calcium), duloxetine (CYMBALTA®; (+)-(S)—N-Methyl-3-(naphthalen-1-yloxy)-3-(thiophen-2-yl) propan-1-amine; administered as duloxetine hydrochloride), fluticasone propionate (S-(fluoromethyl)-6α,9-difluoro-11β, 17-dihydroxy-16α-methyl-3-oxoandrosta-1,4-diene-17β-carbothioate, 17-propanoate; administered in combination with salmeterol xinafoate (ADVAIR DISKUS®)), atorvastatin (LIPITOR®; (3R,5R)-7-[2-(4-Fluorophenyl)-3-phenyl-4-(phenylcarbamoyl)-5-propan-2-ylpyrrol-1-yl]-3,5-dihydroxyheptanoic acid; administered as atorvastatin calcium), chloramphenicol (chloromycetin; 2,2-dichloro-N-[1,3-dihydroxy-1-(4-nitrophenyl)propan-2-yl]acetamide; administered as chloramphenicol sodium succinate), indinavir (CRIXIVAN®; (2S)-1-[(2S,4R)-4-benzyl-2-hydroxy-4-{[(1S,2R)-2-hydroxy-2,3-dihydro-1H-inden-1-yl] carbamoyl}butyl]-N-tert-butyl-4-(pyridin-3-ylmethyl)piperazine-2-carboxamide; administered as indinavir sulfate), entecavir (BARACLUDE®; 2-Amino-9-[(1S,3R,4S)-4-hydroxy-3-(hydroxymethyl)-2-methylidenecyclopentyl]-6,9-dihydro-3H-purin-6-one; administered as entecavir monohydrate), and bedaquiline (SIRTURO®; (1R,2S)-1-(6-

Bromo-2-methoxy-3-quinolyl)-4-dimethylamino-2-(1-naphthyl)-1-phenylbutan-2-ol; administered as bedaquiline fumarate).

All percentages are mole percent, unless indicated otherwise. Enantiomeric excess (ee) is defined as the difference in mole percent of the two enantiomer; for example if two enantiomers are produced in an 80%/20% ration from a reaction, then ee=80%−20%=60%.

DETAILED DESCRIPTION

The present invention makes use of hydridosilatranes as reducing agents for carbonyl and iminium groups (C=N), such as aryl and alkyl carbonyls, aryl and alkyl iminiums, including aldehydes and ketones. Unlike other active reducing agents, the reductions are often tolerant of moisture and air. The reductions may optionally be carried out with an activator, such as a Lewis acid, Lewis base, and Brønsted acid. The reaction may be carried out in a variety of solvent; surprisingly the solvent may be water, and an activator is optional. The reduction is sensitive to steric effects, and provides stereoselective reduction when bulky groups are present within one carbon atom (β) to the carbonyl or iminium carbon. Furthermore, with the use of a chiral activator, such as an amino alkoxide, enantioselective reductions may also be carried out. Alternatively, a chiral hydridosilatrane may also be used to carry out enantioselective reductions.

Figure 8:
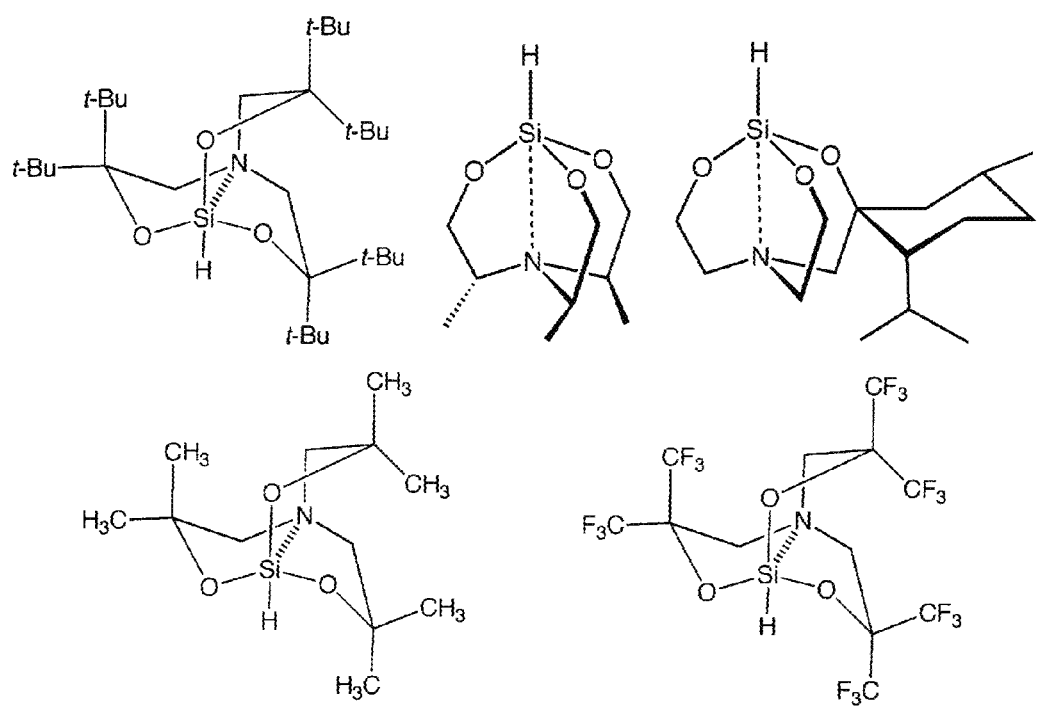
FIG. 8 illustrates examples of hydrosilatranes.

Hydridosilatranes are compounds of formula (I) or formula (II), wherein each $R^1$-$R^{12}$ are independently selected from H, OH, $OR^{13}$, $NR^{14}R^{15}$, aryl, alkyl and alkenyl, and $R^{13}$, $R^{14}$ and $R^{15}$ are each independently selected from H, OH, aryl, alkyl and alkenyl; and pairs of R groups which are bonded to the same carbon atom, together with the carbon atom, form a carbonyl group (C=O). Examples of hydridosilatranes are shown in FIG. 8.

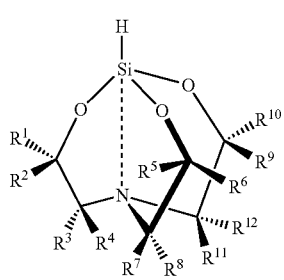

(I)

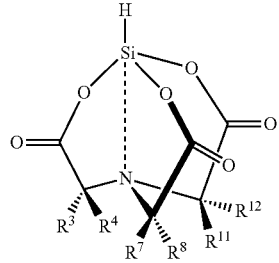

(II)

Preferred hydridosilatranes include those of formulas (I) and (II), wherein $R^3$, $R^4$, $R^7$, $R^8$, $R^{11}$ and $R^{12}$ are H. Preferably, all but a single R group chosen from $R^y$ (y=1 to 12 in formula (I) or y=3, 4, 7, 8, 11 and 12 in formula (II)) are H. Alternatively all but three R groups chosen from $R^y$ (y=1 to 12 in formula (I) or y=3, 4, 7, 8, 11 and 12 in formula (II)) are H, and preferably chosen from —$(CH_2)_xSO_3H$, —$(CH_2)_xNH_2$ and —$(CH_2)_xOH$, where x is an integer from 0 to 6, including 1, 2, 3, 4 and 5; and more preferably the non-H R groups are the same. In another variation, the hydridosilatranes have C3 symmetry. Compound 1 corresponds to all R groups being H. For asymmetric syntheses, preferably the hydridosilatrane is chiral, preferably with at least one R group chosen from $R^y$ (y=1 to 12 in formula (I) or y=3, 4, 7, 8, 11 and 12 in formula (II)) being a bulky group, including 2, 3, 4, 5, 6, 7, 8, 9, 10, 11 or 12 being bulky groups in formula (I), or 2, 3, 4, 5 or 6 being bulky groups in formula (II). Combinations of hydridosilatranes may also be used.

Additional examples of hydridosilatranes include those of formula (I) where 1, 2 or 3 pairs of R groups chosen from $R^y$ (y=1 to 12) which are bonded to the same carbon atom, together with the carbon atom, form a carbonyl group (C=O); and a single R group chosen from $R^y$ (y=1 to 12 in formula (I) or y=3, 4, 7, 8, 11 and 12 in formula (II)) are —OH, —$NH_2$, —$NO_2$ or —$SO_3H$. Each of these hydridosilatranes would be expected to have improved solubility in polar solvents, especially water. Other examples include hydridosilatranes where one to all R groups chosen from $R^y$ (y=1 to 12 in formula (I) or y=3, 4, 7, 8, 11 and 12 in formula (II)) are t-Bu, —$CH_3$, or —$CF_3$.

In a further variation, any of the different hydridosilatranes described above which have 3, 6, 9, or 12 R groups which are not H, may have C3 symmetry. Combinations of any of the different hydridosilatranes described above may also be used.

Hydridosilatranes of formulas (I) and (II) may be formed from a triethanolamine via a corresponding boratrane, using a synthesis similar to that used to prepare compound 1. For example, a triethanolamine may be reacted with boric acid in water; removal of the water by heating may be used to isolate the corresponding boratrane. After purification of the boratrane, for example by recrystallization, it may be reacted with triethoxysilane optionally in the presence of a strong Lewis acid (for example, $AlCl_{3-}$), in a refluxing solvent (for example, xylene) to form a silatrane. The silatrane may be purified by recrystallization from a non-polar solvent, such as xylene.

Many different triethanolamines are commercially available (see below) or may be formed from commercially available triethanolamines (FIG. 9), optionally with the use of a protecting group for —OH groups of the triethanolamine. Additional guidance may be found in the literature.[45, 46, 47]

Examples of commercially available triethanolamines include:

(7) Bicene (N,N-bis(2-hydroxyethyl)glycine) (Acros Organics, Thermo Fisher Scientific, New Jersey),

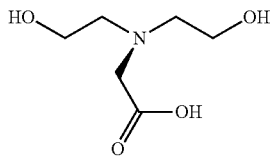

(8) N-(carboxymethyl)-N-(2-hydroxymethyl)glycine (Sigma-Aldrich, St. Louis, Mo.),

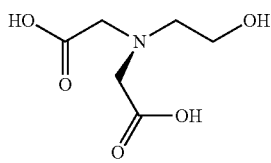

(9) Nitrilotriacetic acid (Acros Organics, Thermo Fisher Scientific, NJ),

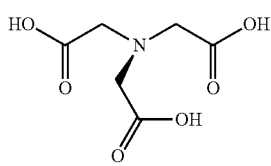

(10) 3-[bis(2-hydroxymethyl)amino]-2-hydroxy-1-propanesulfonic acid (Alfa-Aesar, Thermo Fisher Scientific, NJ),

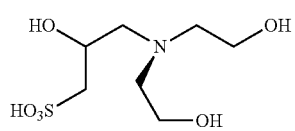

(11) 2-hydroxy-N,N-bis(2-hydroxyethyl)acetamide (Alfa-Aesar, Thermo Fisher Scientific, NJ),

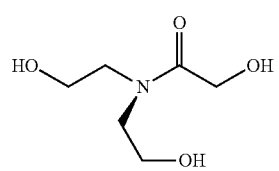

Additional commercially available triethanolamines include (12) 1-amino-3-[bis(2-hydroxyethyl)amino]-2-propanol and (13) 1-[bis(2-hydroxyethyl)amino]-3-dimethylamino-2-propanol (FCH Group, Chernigiv, Ukraine).

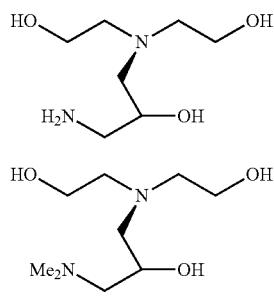

Figure 9:
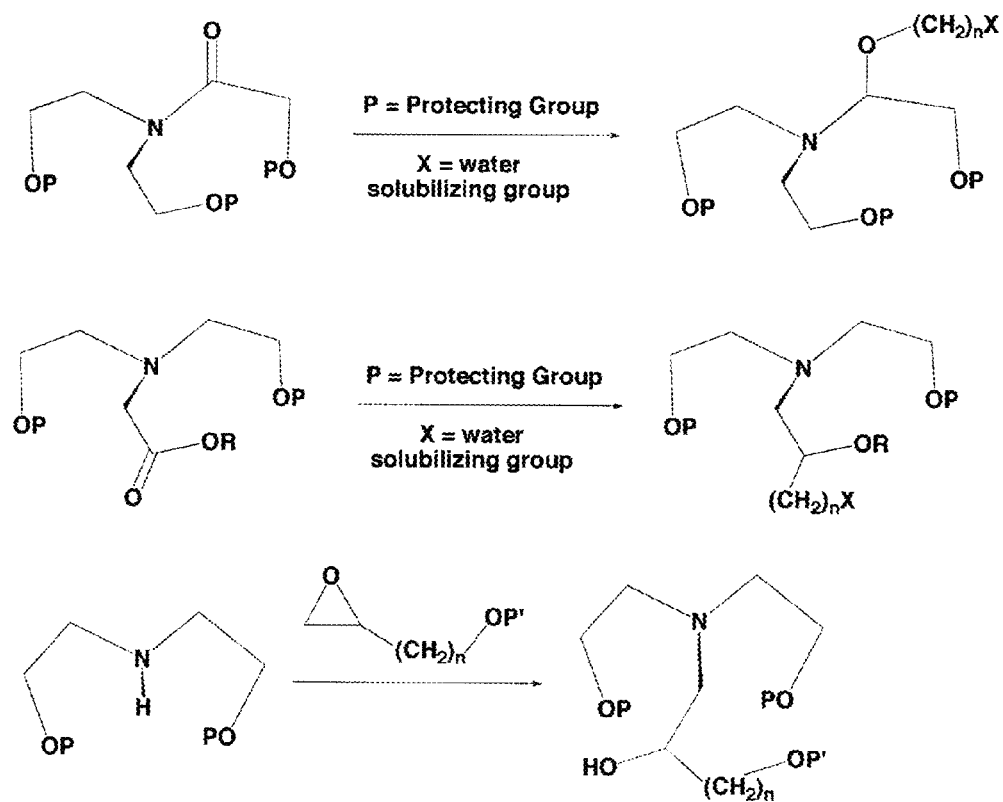
FIG. 9 illustrates reaction schemes for preparing triethanolamines from commercially available triethanolamines.

The triethanolamines above that contain carbonyl functionality may be chemically transformed into other hydrophilic functional groups, which would likely further increase water solubility of the corresponding hydridosilatranes (FIG. 9).

A variety of solvents may be used for the reduction reaction, preferably polar solvents. Unlike many other reducing agents, when using hydridosilatranes there is typically no need for drying, degassing solvents or sealing reactions away from air. However, in some cases it may be desirable to limit exposure of the reactants to air and/or exclude water to prevent competing reactions, such as the oxidation of aldehydes to corresponding carboxylic acids. Examples of polar solvents include dimethylformamide (DMF); tetrahydrofuran (THF); acetonitrile; dichloromethane (DCM); and alcohols such as methanol, ethanol, n-propanol, i-propanol, and ethylene glycol. Non-polar solvents may also be used, including ethers (such as diethyl ether, and diglyme) and alkanes (such as hexane), but they are less desirable.

Surprisingly, water may also be used as a solvent. Although hydridosilatranes may decompose in water, the decomposition reaction may be slow compared to the reduction of aldehydes and ketones. Using hydridosilatranes that contain one or more hydrophilic groups, such as —OH, —$NH_2$, =O, —$NO_2$ and/or —$SO_3H$ may improve water solubility and improve the yield of the reduction reaction. Reductions carried out in water may be carried out with, or without, an activator. Optionally, the water may include salts, such as NaCl, KCl, $MgCl_2$ and/or $CaCl_2$, and in such cases use of a saturated solution of the salt may be desirable.

The use of an activator, such as a Lewis acid, Lewis base, and Brønsted acid is desirable (the oxygen of an ether is not considered to be a Lewis base). Preferably, the activator is a strong base, such as alkali or alkaline earth metal hydroxides, for example sodium hydroxide, potassium hydroxide, and calcium hydroxide; alkoxides, such as potassium t-butoxide and sodium menthoxide; amino alkoxides, such as sodium 1,2-diphenyl-, 2-amino ethoxide; and amide bases, $(NR^aR^b)^-$ where $R^a$ and $R^b$ are independently alkyl or aryl, such as dialkyl amides (for example, lithium diisopropyl amide). In some cases it may be desirable to form the activator in situ by reaction of an alcohol (including amine alcohol) with a hydride, such as NaH. Combinations of activators may also be used. Amines, carbonates and metal salts were not effective as activators for reductions using 1-hydrosilatrane (1).

Enantioselective reduction of prochiral ketones to form chiral alcohols may be carried out by using a chiral activator. Preferably, the chiral activator is an alkoxide of an amino alcohol, such as sodium 1,2-diphenyl-, 2-amino ethoxide. For example, an important intermediate of many pharmaceutical compounds are chiral alcohols. Reduction of a prochiral ketone using a hydridosilatrane with a chiral activator will produce a chiral alcohol, which may then be used to form a pharmaceutical compound. Alternatively, reduction of a prochiral ketone or prochiral iminium using a chiral hydridosilatrane will produce a chiral alcohol or chiral amine, respectively, which may then be used to form a pharmaceutical compound. Example of such pharmaceutical compounds include dorzolamide (TRUSOPT®; (4S,6S)-4-(ethylamino)-6-methyl-7,7-dioxo-5,6-dihydro-4H-thieno[2,3-b]thiopyran-2-sulfonamide; administered as dorzolamide hydrochloride), rosuvastatin (CRESTOR®; (3R,5S,6E)-7-[4-(4-fluorophenyl)-2-(N-methylmethanesulfonamido)-6-(propan-2-yl)pyrimidin-5-yl]-3,5-dihydroxyhept-6-enoic acid; administered as rosuvastatin calcium), duloxetine (CYMBALTA®; (+)-(S)—N-Methyl-3-(naphthalen-1-yloxy)-3-(thiophen-2-yl)propan-1-amine; administered as duloxetine hydrochloride), fluticasone propionate (8-(fluoromethyl)-6α,9-difluoro-11β,17-dihydroxy-16α-methyl-3-oxoandrosta-1,4-diene-17β-carbothioate, 17-propanoate; administered in combination with salmeterol xinafoate (ADVAIR DISKUS®)), atorvastatin (LIPITOR®; (3R,5R)-7-[2-(4-Fluorophenyl)-3-phenyl-4-(phenylcarbamoyl)-5-propan-2-ylpyrrol-1-yl]-3,5-dihydroxyheptanoic acid; administered as atorvastatin calcium), chloramphenicol (chloromycetin; 2,2-dichloro-N-[1,3-dihydroxy-1-(4-nitrophenyl)propan-2-yl]acetamide; administered as chloramphenicol sodium succinate), indinavir (CRIXIVAN®; (2S)-1-[(2S,4R)-4-benzyl-2-hydroxy-4-{[(1S,2R)-2-hydroxy-2,3-dihydro-1H-inden-1-yl]carbamoyl}butyl]-N-tert-butyl-4-(pyridin-3-ylmethyl) piperazine-2-carboxamide; administered as indinavir sulfate), entecavir (BARACLUDE®; 2-Amino-9-[(1S,3R,4S)-4-hydroxy-3-(hydroxymethyl)-2-methylidenecyclopentyl]-6,9-dihydro-3H-purin-6-one; administered as entecavir monohydrate), and bedaquiline (SIRTURO®; (1R,2S)-1-(6-Bromo-2-methoxy-3-quinolyl)-4-dimethylamino-2-(1-naphthyl)-1-phenylbutan-2-ol; administered as bedaquiline fumarate). Preferably such enantioselective reduction reactions result in an ee of at least 20%, more preferably at least 40%, and most preferably at least 60%.

Preferably, the reductions are carried at a temperature of at most 100° C., more preferably at a temperature of at most 80° C., even more preferably at a temperature of at most 60° C.; lower temperatures may be desirable for reduction of aldehydes and ketones, such as a temperature of at most 40° C., even more preferably a temperature of at most 20° C. In some cases, it may be desirable to use a temperature of at most 0° C., or even a temperature of at most −20° C. Most reduction reactions may be carried out at room temperature (about 25° C.). Preferably, the reduction reactions are carried out at a temperature of 0 to 100° C. Preferably, yields of the alcohols or amines are at least 50%, more preferably at least 60%, even more preferably at least 70%, still more preferably at least 71%, still more preferably at least 75%, still more preferably at least 80%, still more preferably at least 85%, still more preferably at least 90%, still more preferably at least 95%, still more preferably at least 98%, still more preferably at least 99% and most preferably 100%, based on the aldehyde, ketone or iminium. In some cases the reduction reaction may be catalytic for the activator, or a molar ration of the activator, to the aldehyde or ketone, is less than 1, more preferably at most 0.5.

The reduction of aldehydes, ketones and iminiums using hydridosilatranes is sensitive to steric effects, and provide stereoselective reductions when bulky groups are present within one carbon atom of the carbonyl carbon of the ketone (that is, 13 position for the bulky group). Preferably, the ketone is a chiral ketone, and one of the two diastereomers will predominate in the reduction products.

Figure 10:
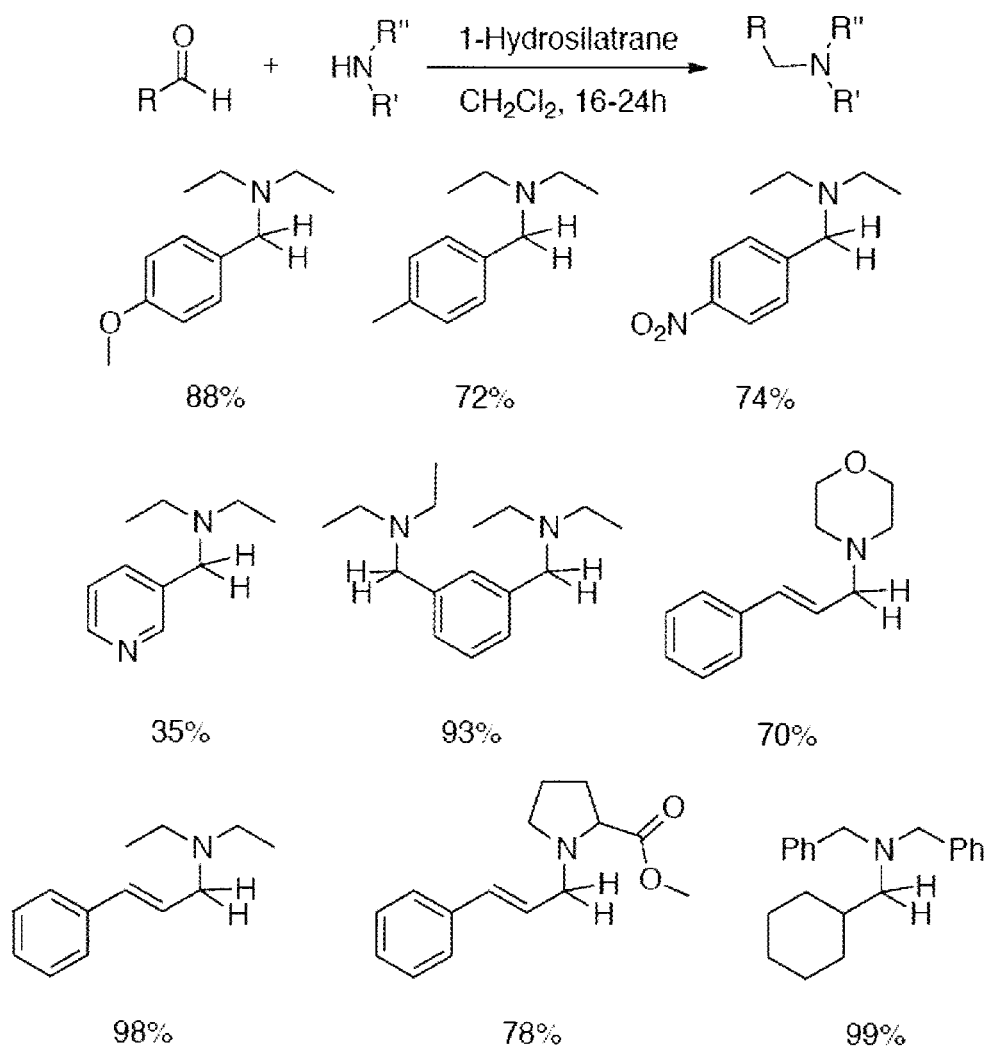
FIG. 10 illustrates yields of reductive amination of various aldehydes (0.5M $CHCl_3$, 60° C., 15-72 h).

The reduction of iminiums using hydridosilatranes is preferably carried out without activators. Such a reaction allows for the one-pot direct reductive amination of an aldehydes or ketones: an amine may react with the carbonyl group, to form an iminium, which is then reduced to an amine by the hydridosilatranes. FIG. 10 illustrates yields of reductive amination of various aldehydes (0.5M CHCl$_3$, 60° C., 15-72 h).

A kit contain a hydridosilatrane, together with an activator, each in separate containers, may be provided. In such a kit, the activator is preferably sodium hydroxide, potassium hydroxide, or t-BuOK.

EXAMPLES

Example 1

Reduction of Aldehydes

Hydrosilatrane is easy to access from inexpensive commercially available substrates and is stable to open air and ambient moisture: 1-hydrosilatrane has been prepared on a multi-gram scale and stored in a snap-top vial that was frequently uncapped for use without any special handling, and under these conditions no detectable degradation occurred over the several-month period of the study. For these reasons, silatrane is an attractive option for a mild and user-friendly reducing reagent and we desired to explore the scope for wider application.

We were unable to reproduce the results of Eaborn and co-workers using either the original or slightly modified conditions.

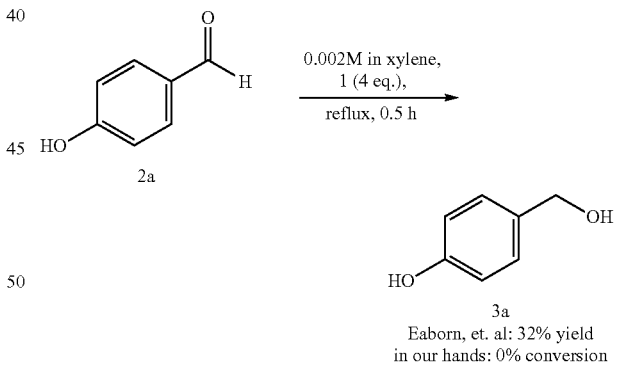

Eaborn, et. al: 32% yield
in our hands: 0% conversion

We chose to examine the reduction of para-anisaldehyde for several reasons: (a) the resulting alcohol has a high enough boiling point to be isolated from high boiling solvents, (b) we believed such electron-rich aryl aldehydes would be more challenging to reduce, and (c) we did not envision any side reaction with aryl-alkyl ethers. This substrate indeed served as a good model reaction.

Solvent screening (Table 1) showed that both DMF and THF were viable solvents for the conversion of 2b to 3b. Solvents were taken directly from a bottle as acquired from the manufacturer and the reaction was set up in an open vessel on the benchtop.

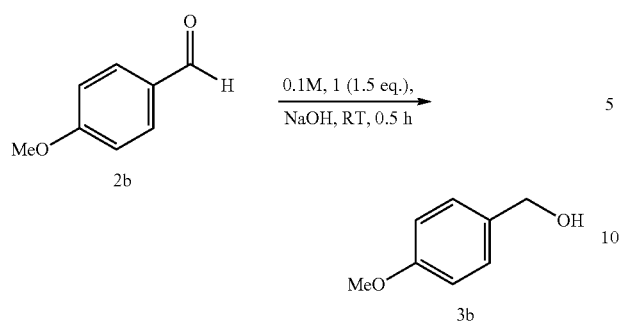

TABLE 1

Solvent screening for the reduction of para-anisaldehyde (2b) with hydrosilatrane (1).

| Entry | Solvent | Yield[a] [%] |
|---|---|---|
| 1 | DMF | 95 |
| 2 | THF | 87 |
| 3 | diethyl ether | 3 |
| 4 | acetonitrile | 30 |
| 5 | hexane | 3 |
| 6 | methanol | 35 |
| 7 | dichloromethane | 81 |

[a]Yield determined by NMR spectroscopy.

We next focused on identifying the mildest possible base to enable the activation of silatrane (Table 2). While both sodium and potassium hydroxide efficiently enabled the conversion of para-anisaldehyde to the corresponding alcohol, no reaction occurred in the presence of other ionic bases. Additionally, basic amines (primary, secondary, and tertiary) failed to spur any reaction under the attempted conditions.

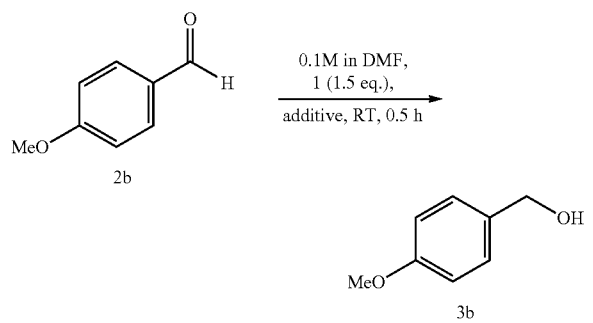

TABLE 2

Additive screening for the reduction of para-anisaldehyde (2b) with hydrosilatrane (1) in DMF.

| Entry | Solvent | Additive | Equiv. of additive | Time (h) | Yield (%) |
|---|---|---|---|---|---|
| 1 | DMF | NaOH | 30 | 0.5 | 95 |
| 2 | DMF | NaOH | 1 | 24 | 53 |
| 3 | DMF | KOH | 20 | 0.5 | 84 |
| 4 | DMF | t-BuOK | 1 | 0.5 | 80 |
| 5 | DMF | iPrNH$_2$ | 1.5 | 1 | 0 |
| 6 | DMF | HNEt$_2$ | 1.5 | 1 | 0 |
| 7 | DMF | NEt$_3$ | 1.5 | 1 | 0 |
| 8 | DMF | CaCl$_2$ | 1.5 | 24 | 0 |
| 9 | THF | NaOH | 30 | 0.5 | 87 |
| 10 | THF | NaHCO$_3$ | 10 | 1 | 0 |
| 11 | THF | Na$_2$CO$_3$ | 10 | 1 | 0 |
| 12 | THF | HCO$_2$Na | 1.5 | 1 | 0 |

Figure 1:
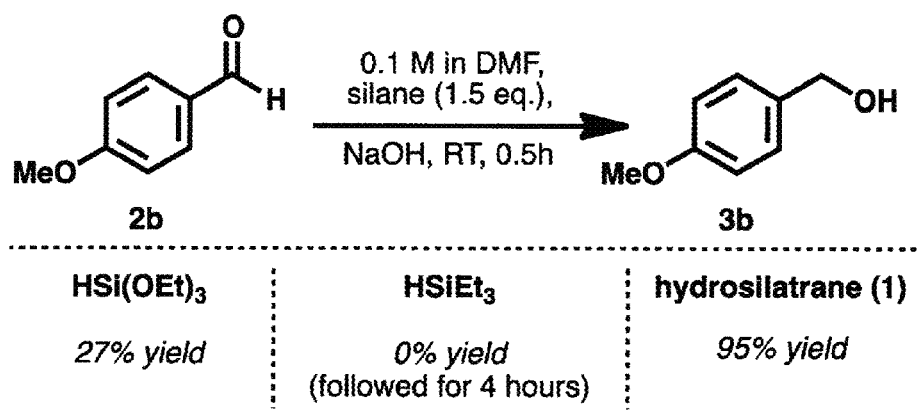
FIG. 1 illustrates reduction reactions using commonly used silane reducing reagents and hydrosilatrane (1).

To demonstrate the unique properties of the silatrane with regard to stability and reactivity, the reaction was attempted with commonly used silane reducing reagents (FIG. 1). The first, triethoxysilane, is a highly reactive species that unsurprisingly quickly degraded in the open-air (and hydroxide-containing) solution following partial reduction of the aldehyde. The second, triethylsilane, is a mild and well-behaved reducing agent, which as expected did not undergo any detectable reaction with the aldehyde under the conditions for the observed period of four hours. The reaction proceeded vigorously and relatively well under the conditions using PMHS (85%), but in the open-air environment silatrane was a more effective reductant.

Finally, the generality of the method was explored: the optimized conditions were applied to a range of commercially available and/or readily synthesized aryl aldehydes (Table 3). Gratifyingly, unsubstituted benzaldehyde 2c was reduced in excellent yield (Entry 1). Electron-rich aryl aldehydes (e.g. 2d and 2h) also were efficiently reduced, even when the substituent was in the meta (2f) or ortho position (2g).

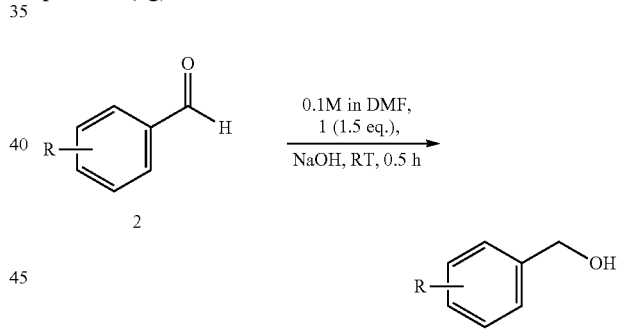

TABLE 3

Reduction of substituted benzaldehydes 2 with hydrosilatrane (1).

| Entry | R | Aldehyde/alcohol | Yield[a] (%) |
|---|---|---|---|
| 1 | H | 2c/3c | 98[b] |
| 2 | 4-t-Bu | 2d/3d | 95 |
| 3 | 4-Me | 2e/3e | 66[c] |
| 4 | | | 92[b,d] |
| 5 | 4-OMe | 2b/3b | 95 |
| 6 | 3-OMe | 2f/3f | 96 |
| 7 | 2-OMe | 2g/3g | 88 |
| 8 | 4-OPh | 2h/3h | 94 |
| 9 | 4-OBn | 2i/3i | 99 |
| 10 | 4-OAll | 2j/3j | 98 |
| 11 | 4-CN | 2k/3k | 60[c] |
| 12 | | | 93[b,d] |

TABLE 3-continued

Reduction of substituted benzaldehydes 2 with hydrosilatrane (1).

| Entry | R | Aldehyde/alcohol | Yield[a] (%) |
|---|---|---|---|
| 13 | 3-NO2 | 2l/3l | 88[c] |
| 14 | 4-Cl | 2m/3m | 76[c] |
| 15 | | | 98[b,d] |
| 16 | 4-F | 2n/3n | 98[b,d] |
| 17 | 3-F | 2o/3o | 28[c] |
| 18 | | | 99[b,d] |
| 19 | 2-F | 2p/3p | 46[c] |
| 20 | | | 96[b,d] |
| 21 | 4-OH | 2a/3a | 0 |
| 22 | | | 0[e] |
| 23 | 3-OH | 2q/3q | 44 |
| 24 | | | 36[e] |

[a]Yield determined by NMR unless otherwise noted.
[b]Yield determined by GC-FID.
[c]Product mixture contained significant amounts (>5%) of corresponding benzoic acid.
[d]Reaction run under oxygen-free conditions.
[e]Reaction run with 2.5 equiv. of 1 for 24 h.

While aldehydes bearing electron-withdrawing groups (including 2k, 2l, and 2m) were well tolerated, the alcohol product was generally accompanied by significant amounts of the corresponding benzoic acid in the crude product mixture. This observation suggested that either (a) Cannizaro reaction[17] and/or (b) aerobic oxidation were concurrently taking place. The deleterious benzoic acid product was also formed in the attempted reduction of 2e. Reactions run with 2e, 2k, 2m, and 2o in the absence of silatrane showed conversion to mixtures of alcohol and carboxylic acid, with the acid being the predominant species; these results indicate that both side reactions may be taking place. In order to minimize the contribution of aerobic oxidation to the generation of unwanted benzoic acid, several substrates were run under oxygen-free conditions; these trials provided clean reductions and no observable benzoic acid (Entries 4, 12, 15, 16, 18, and 20).

Under the investigated conditions, hydrosilatrane (1) exhibited no reaction with other reducible functionalities examined, including the nitriles (Entries 11, 12), nitro group (Entry 15), benzyl (Entry 9) and allyl ethers (Entry 10), and halides (Entries 14-20).

Hydroxybenzaldehydes were unfortunately not reduced effectively: while 3-hydroxy-(2q, Entry 23) was partially reduced using the described method, 4-hydroxybenzaldehyde (2a, Entry 21) remained unmoved. In these cases, bubbling is observed initially, which is consistent with an acid/base reaction occurring between the hydride of the silatrane and the proton of the phenol.[18] Reduction may then occur, though the anionic benzaldehyde substituent significantly decreases the electrophilicity of the aldehyde; this results in decreased reactivity of the meta variant (2q) and no reaction at all in the para derivative (2a). Yields in both cases were not affected by increasing both the concentration of silatrane and reaction time (Entries 22, 24).

Figure 3:
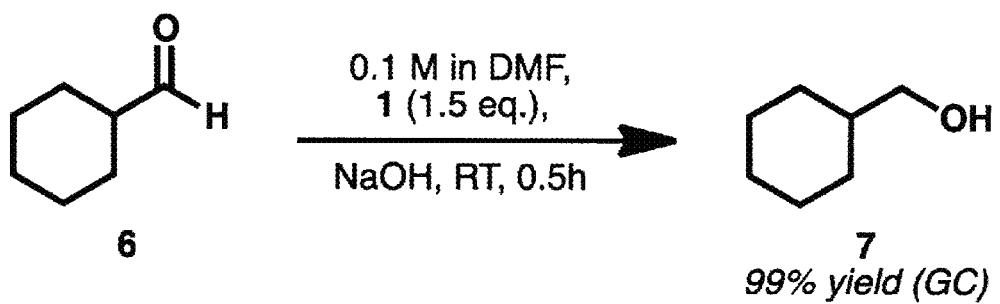
FIG. 3 illustrates a reaction scheme for reduction of an aliphatic aldehyde.
Figure 2:
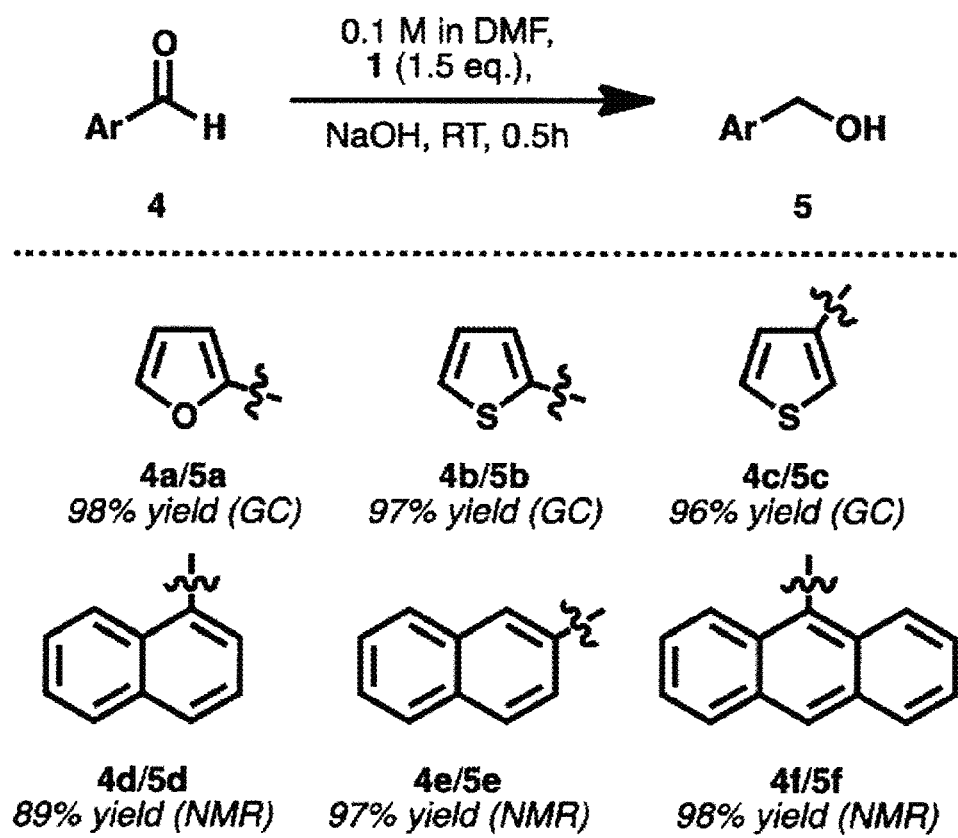
FIG. 2 illustrates the products and yields of reductions of heteroatom-containing and polycyclic aryl aldehydes.

The method was also applied to heteroatom-containing (4a, 4b, and 4c) and polycyclic (4d, 4e, and 4f) aryl aldehydes. In all cases, the reaction proceeded as expected with excellent yields and no observation of side products (FIG. 2). This method was also proven to be effective on aliphatic aldehyde 6 (FIG. 3).

Conclusions

Cheap and easily accessible hydrosilatrane has been shown to be an effective reductant of aldehydes bearing a variety of functionalities in this user-friendly method. Furthermore, hydrosilatrane demonstrates excellent stability to air and ambient moisture rendering it amenable to benchtop reactions and long-term storage.

Experimental Section

General Considerations

All reactions were carried out under ambient conditions in an open vessel, with no special effort to exclude water or air from reaction mixtures unless otherwise noted. Chemicals and reagents were purchased from Sigma-Aldrich and/or Fisher, and were used without further purification unless otherwise noted. 1H NMR spectra were recorded at 500/300 MHz at ambient temperature using a Bruker Avance III spectrometer. The chemical shifts in 1H NMR spectra are reported relative to residual $CHCl_3$ in $CDCl_3$ ($\delta$=7.27 ppm). The chemical shifts in 13C NMR spectra are reported relative to residual $CHCl_3$ in $CDCl_3$ ($\delta$=77.23 ppm). The yields were determined using mesitylene as an internal standard in $CDCl_3$. The abbreviations used for the chemical shifts are as follows: s (singlet), d (doublet), t (triplet), dd (doublet of doublets), dt (doublet of triplets), td (triplet of doublets), dq (doublet of quartets), m (unresolved multiplet).

Synthesis of Silatrane Via Boratrane

To a 25 mL flask was added boric acid (50 mmol) and triethanolamine (50 mmol). Water (3 mL) was added to facilitate solubility. The flask was equipped with a short path distillation apparatus and heated to 120° C. until no more water condensed. The isolated boratrane was recrystallized from acetonitrile and used directly in the next step. The experimental data collected are in agreement with those described in the literature.[1] 70%. 1H NMR (500 MHz, $CDCl_3$): $\delta$=3.65 (t, J=5.5 Hz, 6 H), 3.04 (t, J=5.5 Hz, 6 H). 13C NMR (125 MHz, $CDCl_3$) 62.1, 59.3. IR (ATR) 2988, 2853, 1469, 1370, 1258, 1160, 1115, 1063, 1026, 1001, 933, 889, 730, 621, 560.

To an oven-dried, argon-flushed 100 mL flask containing boratrane (5 mmol) in mixed xylenes (40 mL), was added triethoxysilane (6 mmol) and anhydrous $AlCl_3$ (0.05 mmol). The reaction was refluxed over 4 h and then cooled to room temperature. The resulting solids were filtered and further recrystallized from xylene to give silatrane as white fibrous crystals. The experimental data collected are in agreement with those described in the literature.[19] 88%. 1H NMR (500 MHz, $CDCl_3$): $\delta$=3.94 (s, 1 H), 3.83 (t, J=6 Hz, 6 H), 2.89 (t, J=6 Hz, 6 H). 13C NMR (125 MHz, $CDCl_3$) 57.2, 51.2. IR (ATR) 2975, 2936, 2886, 2087, 1487, 1457, 1347, 1268, 1090, 1047, 1020, 926, 860, 748, 630, 591.

General Method for the Reduction of Aldehydes:

To a 2 dram vial containing a stir bar was added silatrane (0.15 mmol), aldehyde (0.1 mmol), and DMF (1 mL). The solution was stirred for 5 min to allow for all the silatrane to dissolve, after which additive (1 pellet of NaOH finely ground) was added. After 30 min of stirring in ambient conditions the solution was washed once with 1 M HCl, then extracted three times with dichloromethane and once with diethyl ether. The resulting organic extract was concentrated under reduced pressure and used to determine yield without any further purification. All of the alcohols synthesized are known compounds.

Example 2

Reduction of Ketones

Herein we discuss the activation of 1-hydrosilatrane with a strong Lewis base to reduce ketones, the scope of the reaction, and stereoselectivity and enantioselectivity in the process.

Acetophenone 2a was reduced in N,N-dimethylformamide at room temperature within 70 minutes using 1.1 equivalents of 1-hydrosilatrane in the presence of 1 equivalent of potassium tert-butoxide, giving 94% conversion to 1-phenylethanol 3a (Table 4, entry 1). Tests of different solvents (Table 4, entries 2-4) indicated that the more polar the solvent, the greater the yield of alcohol from ketone. This appears due to the fact that 1 is more soluble in polar solvents.

Substitution of sodium hydroxide for tert-butoxide (Table 4, entry 5) induced reduction of acetophenone 3a, but with low conversion. Excess amounts of sodium hydroxide in optimized conditions gave higher yields, but these still were not as good as with tert-butoxide. Milder Lewis bases (Table 4, entries 6-7) gave no conversion, indicating the need of a strong base to activate 1. Lowering the amount of tert-butoxide to 0.5 equivalents gave lower yields (Table 4, entry 8). When 2-methoxyacetophenone 2b was treated with 1 and 0.5 equivalents of tert-butoxide for 48 h, the yield of alcohol 3b was 100%, implying that in this case the activator acted catalytically.

TABLE 4

Selection of solvents and activators for reaction

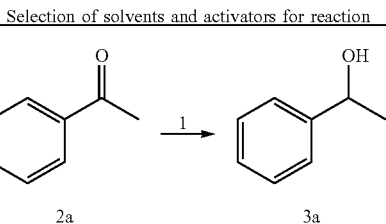

| | Activator | Eq. activator | Eq. 1 | Solvent | Time (min.) | Yield (%) |
|---|---|---|---|---|---|---|
| 1 | t-BuOK | 1 | 1.1 | DMF | 40 | 94 |
| 2 | t-BuOK | 1 | 1.1 | DCM | 40 | 81 |
| 3 | t-BuOK | 1 | 1.1 | MeCN | 40 | 74 |
| 4 | t-BuOK | 1 | 1.1 | THF | 40 | 15 |
| 5 | NaOH | 1 | 1.5 | DMF | 70 | 22 |
| 6 | K$_2$CO$_3$ | 1 | 1.5 | DMF | 70 | 0 |
| 7 | TEA | 1 | 1.5 | DMF | 70 | 0 |
| 8 | t-BuOK | 0.5 | 1.1 | DMF | 70 | 20 |

Figure 4:
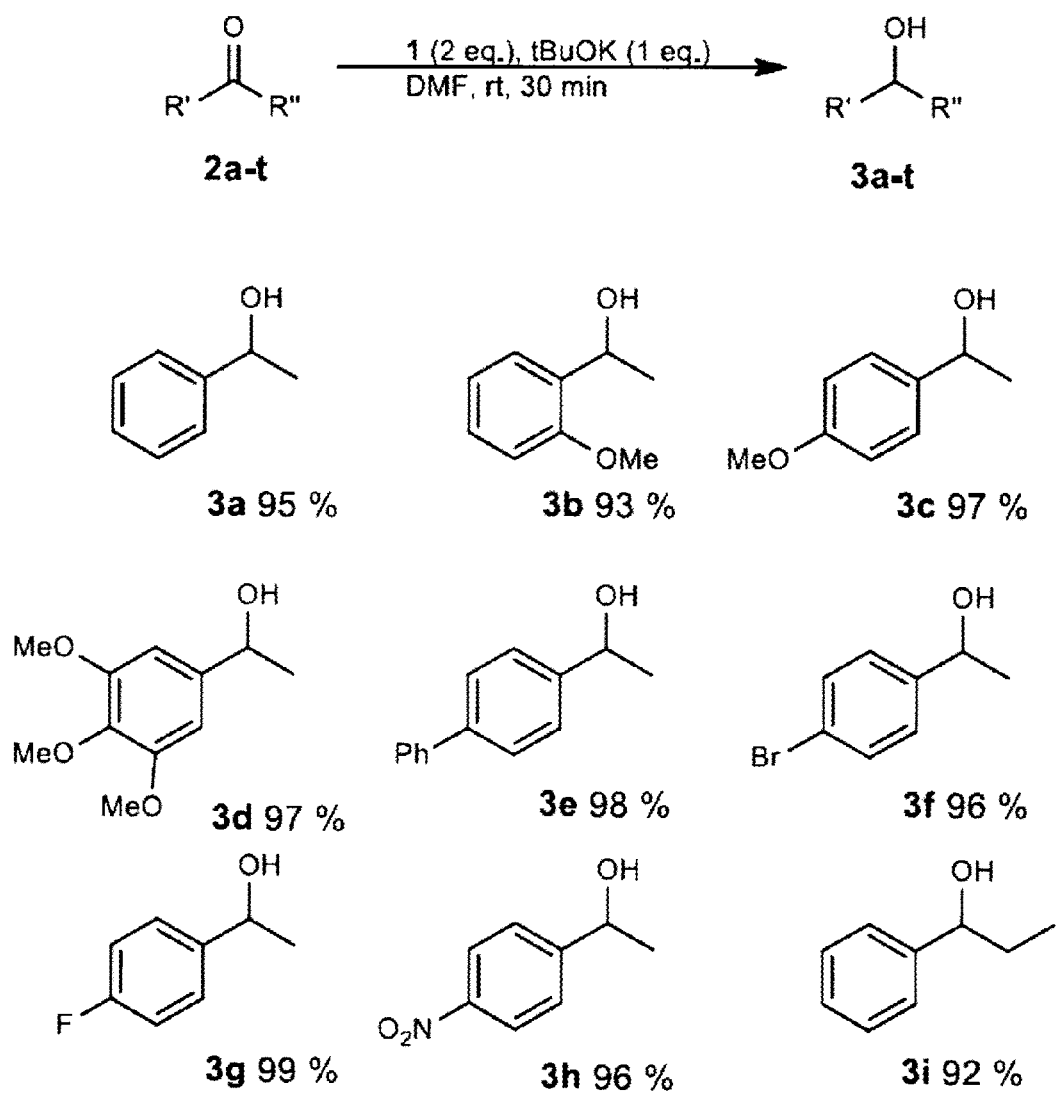
FIG. 4 and FIG. 5 illustrate yields of reductions of various ketones.
Figure 5:
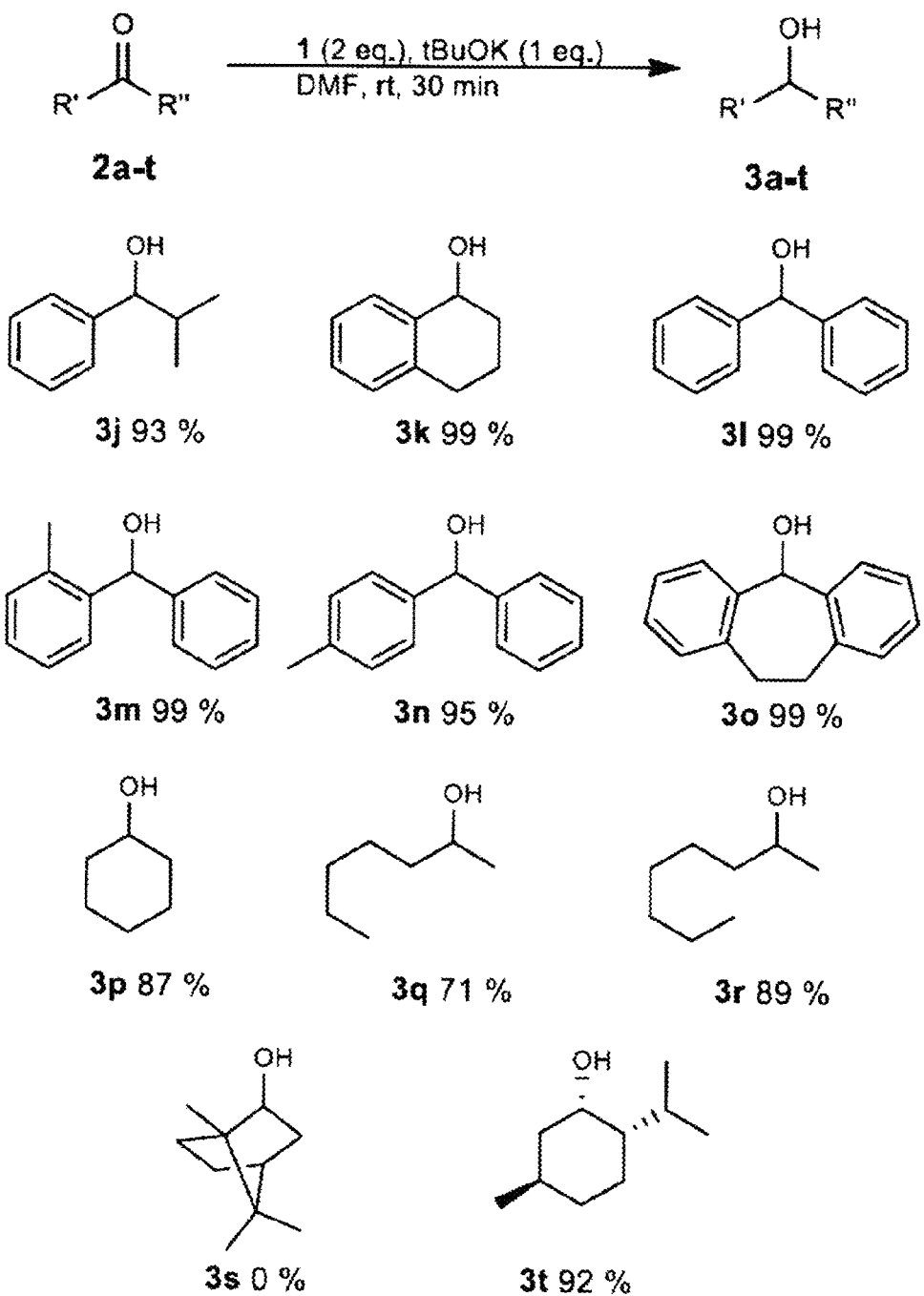

The scope of this reaction is very broad, as seen in FIG. 4 and FIG. 5. Electron donating groups such as methoxy and phenyl as in 3b-e, inductively electron withdrawing groups such as halides as in 3f-g, and strong electron withdrawing groups such as nitro groups as in 3h give excellent yields. Changing the substituents on the alpha position is fully tolerated as in 3i-k, even with phenyl groups as in 3l-o. The system is not limited to phenylketones, as can be seen with the reduction of cyclohexanone 3p, heptanone 3q, and octanone 3r. The isolated yields for the aliphatic alcohols may be lower due to their increased water solubility and hence lower recovery during work up.

Figure 6:
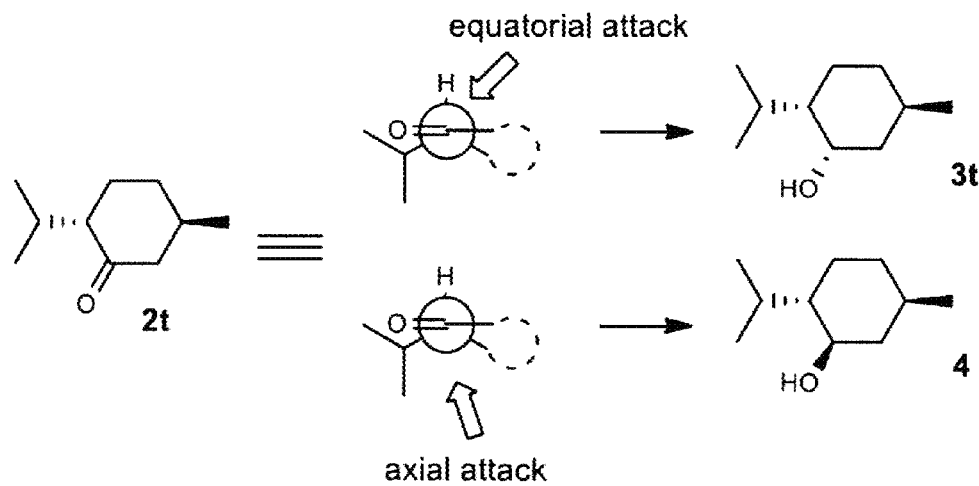
FIG. 6 illustrates steric effects during reduction of menthone using hydrosilatrane (1).

The system, however, is limited by steric effects, as can be seen by the inability of 1-hydrosilatrane to reduce the sterically hindered carbonyl in camphor 3s. This steric limitation was used to reduce (−)-menthone 2t stereoselectively, with great success. The product is almost exclusively (+)-neomenthol 3t (FIG. 6).

A survey of the literature shows that there are only a few compounds with such high selectivity for a single diastereomer in the reduction of (−)-menthone 2t, and out of those, few favor the thermodynamically less stable (+)-neomenthol 3t (Table 5). Unlike reductions using certain bulky reducing agents where the diastereoselectivity is solvent dependent, [35] we do not see a significant difference in our selectivity when the solvent is changed from a polar solvent, DMF (Table 5, entry 8), to a nonpolar solvent such as toluene (Table 5, entry 9). This is likely due to the bulk of the 1-hydrosilatrane 1, which can only approach the (−)-menthone 2t from the less sterically hindered face in an equatorial attack, giving the resulting product 3t.

TABLE 5

Stereoselectivity of the reduction of menthone

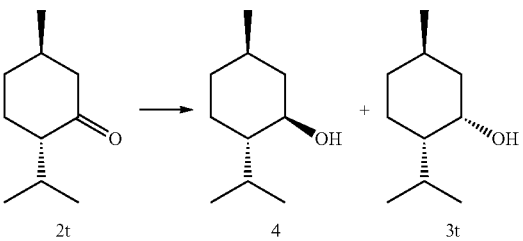

| | Reducing Agent | 4:3t | Ref. |
|---|---|---|---|
| 1 | NaBH$_4$ | 35:65 | [38] |
| 2 | LiB(C$_2$H$_5$)$_3$H | 10:90 | [38] |
| 3 | LiAlH$_4$ | 72:28 | [39] |
| 4 | Al(i-PrO)(i-Bu)$_2$H | 1:99 | [35] |
| 5 | PMHS/TBAF/Pcy | 40:60 | [40] |
| 6 | Pt/C•H$_2$ | 19:81 | [41] |
| 7 | B(C$_6$H$_5$)$_3$/H$_2$ | 100:0 | [42] |
| 8 | 1-Hydrosilatrane/t-BuOK$^a$ | 3:97 | |
| 9 | 1-Hydrosilatrane/t-BuOK$^b$ | 1:99 | |

This stereoselectivity of the reduction of menthone 2t, as well as the inability to do so with camphor, suggests that the reaction is concerted between the hydride donor, 1, and the carbonyl. The increased solubility of 1 in the presence of an activator, and the need for an activator for a reduction to occur efficiently, allows us to propose a possible mechanism. The Lewis base activator coordinates with the silicon, breaking the dative bond between silicon and nitrogen, maintaining the silicon as pentacoordinate.

The silicon then forms a hexacoordinate complex with the carbonyl, at which point the hydride is transferred to the electrophilic carbon center to reform pentacoordinate silicon.[26c, 37] This goes on to collapse by elimination of the Lewis base activator to form the alkoxysilatrane. Support for this possible mechanism arises from the observation that when acetophenone is reduced in the presence of tert-butoxide activator, 1-(phenylethoxy)silatrane can be seen on the GCMS trace and in the 1H NMR spectrum after neutral workup.

Figure 7:
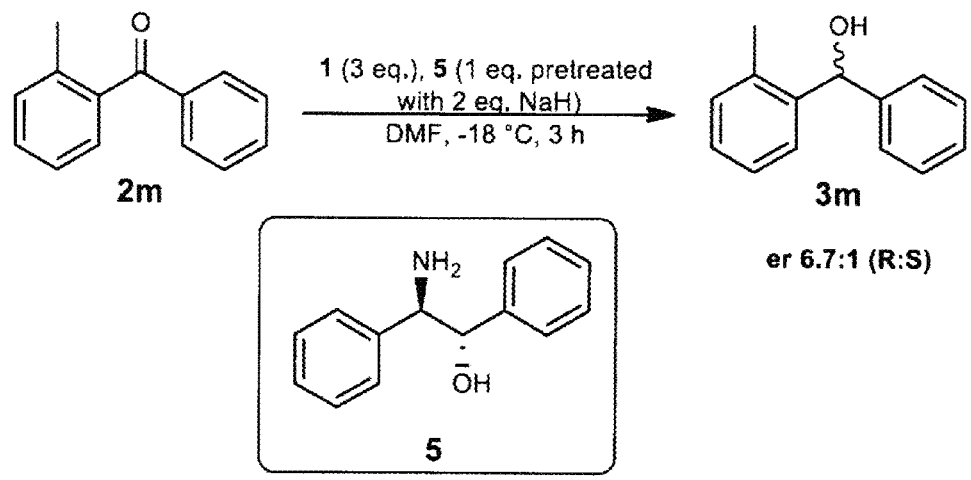
FIG. 7 illustrates a reaction scheme for an enantioselectivity reduction of a prochiral ketone using a chiral activator.

Due to the steric constraints of the system, a chiral activator can provide enantioselectivity with prochiral ketones. If the alkoxide product remains attached to the silatrane, interference of said product as a less selective activator is minimized.[26a] (1S,2R)-(+)-1,2-diphenyl-2-amino-1-ethanol 5, was deprotonated with sodium hydride and used in situ as an activator for 1 in the reduction of 2-methylbenzophenone 2m. This gave a respectable enantiomeric ratio of 6.7:1 (FIG. 7).

In summary, we have reduced a broad range of ketones with 1-hydrosilatrane 1 in excellent yields. High diastereoselectivity of the reduction of (−)-menthone 2t to (+)-neomenthol 3t was observed, consistent with a bulky reducing intermediate. Enantioselectivity was observed for the reduction of the prochiral 2-methylbenzophenone 2m with 1 and a chiral activator.

Experimental Section

General Considerations

With the exception of sodium hydride (which was washed with hexanes) and 1-hydrosilatrane (1), all chemicals were obtained from commercial sources and used without further purification. Column chromatography was performed using silica gel from Macherey-Nagel (60 M, 0.04-0.063 mm). $^1$H NMR, and $^{13}$C NMR were recorded on either a 300 or 500 MHz Bruker Avance III spectrometer. Chemical shifts were reported in ppm with the solvent resonance as internal standard ($^1$H NMR CDCl$_3$ $_{\delta=7.28}$, $^{13}$C NMR CDCl$_3$ $\delta=77.01$, $^{13}$C NMR (CD$_3$)$_2$SO $\delta=39.99$). The abbreviations used for the chemical shifts are as follows: s (singlet), d (doublet), t (triplet), dd (doublet of doublets), dddd (doublet of doublet of doublet of doublets), dt (doublet of triplets), td (triplet of doublets), dq (doublet of quartets), oct (octet), m (unresolved multiplet). IR spectra were acquired using an ATI Mattson FTIR spectrophotometer on neat samples. MS data were obtained with a Shimadzu GCMS QC2010S spectrometer at 275° C. Optical rotation was obtained with a JASCO P1010 polarimeter, running a Na lamp at $\lambda=589$ nm. Enantiomeric ratios (er) were obtained by comparing the observed optical rotation to literature precedence.

General Procedure for the Reduction of Ketones

To a 25 ml round bottom flask containing 5 ml N,N-dimethylformamide, was added 1-hydrosilatrane (0.263 g, 2.0 mmol), and ketone (1.0 mmol). The resulting solution was stirred for 1 minute, after which 1 M t-BuOK in THF (1.0 mmol, 1.0 ml) was added. Reaction mixture was allowed to stir for 30 min. Reaction was quenched with 25 ml 3 M HCl, and extracted with 30 mL ethyl acetate. Organic layer was washed with brine (50 ml×3), and dried with anhydrous sodium sulphate. After filtration, the solvent was removed under vacuum to yield product.

General Procedure for the Asymmetric Reduction of Ketones

To a flame dried 25 mL round bottom flask, under argon, was added 10 mL N,N-dimethylformamide, (1S,2R)-(+)-2-amino-1,2-diphenylethanol (0.213 g, 1.0 mmol), and sodium hydride (0.052 g, 2.2 mmol). Reaction mixture was stirred and gently warmed until a colour change from cream to yellow was observed. A further colour change to deep red was observed as the reaction mixture was cooled down to −18° C. using dichlorobenzene/N$_2$ slurry. 1-Hydrosilatrane (0.526 g, 3.0 mmol) was added to the reaction mixture, followed by 2-methylbenzophenone (0.18 ml, 1.0 mmol). Reaction was allowed to stir for 3 h before it was quenched with 3 M HCl (25 ml). Extraction was done with a 1:1:1 solution of ethyl acetate/diethyl ether/dichloromethane. The organic layer was washed sequentially with 3 M HCl (25 ml), and brine (25 ml×3), before it was dried with anhydrous sodium sulphate. After filtration, the solvent was removed under vacuum to give solid product (2-methylphenyl)(phenyl)methanol.

TABLE 6

Selection of solvents and activators for reactions

| | Ketone | Activator | Activator equiv | Silatrane equiv | Solvent | Rxn time | Conversion (% by GC) |
|---|---|---|---|---|---|---|---|
| 1 | Acetophenone | t-BuOK | 1.0 | 1.1 | THF | 40 min | 15 |
| 2 | Acetophenone | t-BuOK | 1.0 | 1.1 | DMF | 40 min | 94 |
| 3 | Acetophenone | t-BuOK | 1.0 | 1.1 | MeCN | 40 min | 74 |
| 4 | Acetophenone | t-BuOK | 1.0 | 1.1 | DCM | 40 min | 81 |
| 5 | Acetophenone | AlCl$_3$ | 1.0 | 1.1 | DMF | 70 min | 0 |
| 6 | Acetophenone | CuCl$_2$ | 1.0 | 1.1 | DMF | 70 min | 0 |
| 7 | Acetophenone | NaOH | Pellet | 1.1 | DMF | 70 min | 35 |
| 8 | Acetophenone | t-BuOK | 0.5 | 1.1 | DMF | 70 min | 20 |
| 9 | Acetophenone | NaOH | 1.0 | 1.5 | DMF | 70 min | 22 |
| 10 | Acetophenone | K$_2$CO$_3$ | 1.0 | 1.5 | DMF | 70 min | 0 |
| 11 | Acetophenone | TEA | 1.0 | 1.5 | DMF | 70 min | 0 |
| 12 | Acetophenone | NaOH | Pellet (crushed) | 1.5 | DMF | 70 min | 86 |
| 13 | Acetophenone | NaOH | Pellet (crushed) | 2.0 | DMF | 70 min | 82 |
| 14 | Acetophenone | KOH | Pellet (crushed) | 1.5 | DMF | 70 min | 42 |
| 15 | 4-Methoxyacetophenone | t-BuOK | 1.0 | 1.5 | DMF | 70 h | 66 |
| 16 | 4-Methoxyacetophenone | t-BuOK | 1.0 | 1.5 | DMF | 110 min | 95 |
| 17 | 4-Methoxyacetophenone | NaOH | 1.0 | 1.5 | DMF | 110 min | 43 |
| 18 | Acetophenone | t-BuOK | 1.0 | 1.5 | DMF | 70 min | 100 |
| 19 | Acetophenone | NaOH | exs | 2.0 | DMF | 75 min (60° C.) | 52 |
| 20 | Acetophenone | NaOH | exs | 2.0 | DMF | 10 min (60° C.) | 15 |
| 21 | Acetophenone | NaOH | exs | 2.0 | DMF | 20 min (60° C.) | 37 |
| 22 | Acetophenone | NaOH | exs | 2.0 | DMF | 40 min (60° C.) | 42 |
| 23 | 4-Methoxyacetophenone | t-BuOK | 1.0 | 2.0 | DMF | 35 min | 100 |
| 24 | 2-Methoxyacetophenone | t-BuOK | 1.0 | 1.5 | DMF | 35 min | 90 |
| 25 | 2-Methoxyacetophenone | t-BuOK | 1.0 | 2.0 | DMF | 30 min | 100 |
| 26 | 2-Methoxyacetophenone | t-BuOK | 0.5 | 2.0 | DMF | 70 h | 100 |
| 27 | Acetophenone | Ti(Oi-Pr)$_4$ | 1.0 | 2.0 | DMF | 30 min | 0 |

Example 3

Reduction of Aldehydes in Water

To a 10 mL round bottom flask was added 0.11 mmol of 1-hydrosilatrane, 0.1 mmol 4-methoxybenzaldehyde and 1 mL of deionized water. The solution was stirred for 6h. This was then quenched by 1M HCl and extracted three times with DCM. The combined extracts were concentrated and yield was determined using NMR with internal standard. The procedure was also carried out using a saturate solution of NaCl in water, in place of the deionized water.

Example 4

Asymmetric Reduction of Ketones Using Mentholate

To a 25 mL round bottom flask flame dried under argon was added (L)-Menthol 1.0 mmol, DMF 5 mL and 1.05 mmol of sodium hydride. The solution was left stirring until hydrogen evolution stopped. The resulting mixture was cooled to −45° C. at which time 2.0 mmol of 1-hydrosilatrane and 1.0 mmol of Isobutyrophenone was added. The solution was stirred at −45° C. over 4h and then allowed to warm up to room temperature. The reaction was quenched with 1M HCl and extracted with three times with DCM. The combined extracts were concentrated and purified using column chromatography with 2/1 hexane ether as the eluent. (ee 1.12%).

To a 10 mL round bottom flask flame dried under argon was added (L)-Menthol 1.0 mmol, DMF 5 mL and 2 mmol of sodium hydride. The solution was heated to 100° C. and left stirring until all the hydrogen evolution stopped. The resulting mixture was cooled to 0° C. upon which 3 mmol of 1-hydrosilatrane and 1 mmol of methylbenzophenone were added. The solution was left to stir at 0° C. over 30 min and than allowed to warm up to room temperature. The reaction was quenched with 1 M HCl and extracted with three times with DCM. The combined extracts were concentrated and purified using column chromatography with 4/3/1 hexane/toluene/ethyl ether as the eluent. (ee 22%).

Example 5

Reductive Amination of Aldehydes

1-Hydrosilatrane (1.0 mmol), chloroform (2 mL), aldehyde (1.1 mmol), and amine (1.0 mmol) were added to an 8 mL vial, and stirred at 60° C. for 20 h. The reaction mixture was quenched with 1M HCl (20 mL) and extracted with diethyl ether (20 mL×2). The aqueous layer was basified with 6M NaOH (10 mL) and extracted with dichloromethane (20 ml×4), after which the dichloromethane extractions were combined, dried with $Na_2SO_4$, filtered, and distilled in vacuo to give product.

Example 6

Reductive Amination of Ketones

1-Hydrosilatrane (2.2 mmol), acetophenone (2.5 mmol), chloroform (0.2 mL), and pyrrolidine (1.0 mmol) were added to an 8 mL vial, and stirred at 60° C. for 20 h. The reaction mixture was quenched with 1M HCl (20 mL) and extracted with diethyl ether (20 mL×2). The aqueous layer was basified with 6M NaOH (10 mL) and extracted with dichloromethane (20 ml×4), after which the dichloromethane extractions were combined, dried with Na2SO4, filtered, and distilled in vacuo to give product.

Example 7

Synthesis of a Chiral Boratrane

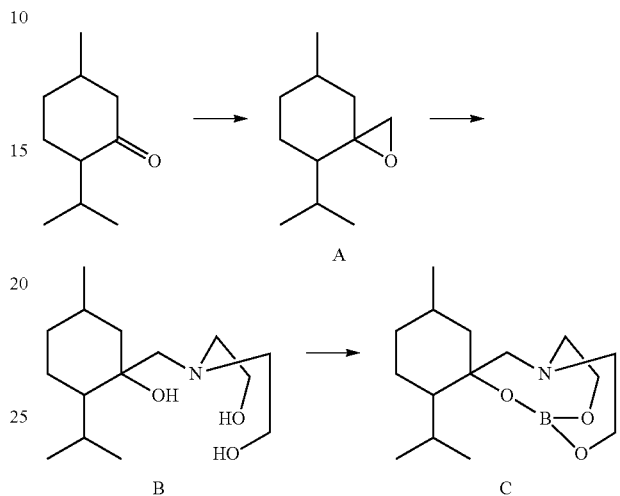

Trimethylsulfoxonium iodide (21 mmol), DMSO (15 mL), and Sodium Hydride (21 mmol) were added to an oven dried 50 mL round bottom flask, and the reaction mixture was stirred vigorously under an argon atmosphere for 2 h. The reaction mixture was cooled to 0° C. in an ice bath and menthone (20 mmol) dissolved in DMSO (5 mL) was added dropwise over 10 minutes. The flask was covered in foil and allowed to stir for 14 h. The reaction mixture is poured onto ice (80 g) and the resulting slurry is extracted with diethyl ether (3×40 mL). The organic phase was washed with brine (2×20 mL), dried with $MgSO_4$, filtered, and distilled in vacuo to obtain crude product A, which was used without further purification.

Product A was mixed with diethanolamine (20 mmol) and the resulting mixture was heated at 120° C. for 96 h, after which it was cooled down to room temperature and placed under high vacuum for 5 h, to give crude Product B, which was used without further purification. (Synthesis of A adapted from Duran et al.[50])

Product B was added to a solution of boric acid (19.5 mmol) in water (25 ml), and the mixture was stirred at 117° C. for 6 h. Reaction mixture is allowed to cool down for maximum amount of white solid to precipitate, which is filtered and recrystallized from acetonitrile to give pure product C (44% yield). (Synthesis of B adapted from Wagner et al.[51]).

The corresponding hydridosilatrane may be produced by reacting product C with triethoxysilane and anhydrous $AlCl_3$.

REFERENCES

[1](a) H. I. Schlesinger, C. H. Brown, A. E. Finholt, R. J. Gilbreath, R. H. Hoekstra, K. E. Hyde, J. Am. Chem. Soc. 1953, 75, 215-219; (b) H. I. Schlesinger, C. H. Brown, B. Abraham, A. C. Bond, N. Davidson, A. E. Finholt, R. J. Gilbreath, H. Hoekstra, L. Horvitz, K. E. Hyde, J. Am. Chem. Soc. 1953, 75, 186-190.

[2] G. L. Larson, J. L. Fry, *Org. React.* 2008, 71, 1-737.

[3] (a) Z. Jia, M. Liu, X. Li, A. S. C. Chan, C.-J. Li, *Synlett* 2013, 24, 2049-2056; (b) M. Fujita, T. Hiyama, *J. Org. Chem.* 1988, 53, 5405-5415; (c) M. P. Doyle, D. J. DeBruyn, S. J. Donnelly, D. A. Kooista, A. A. Odubeta, C. T. West, S. M. Zonnedelt, *J. Org. Chem.* 1974, 39, 2740-2747.

[4] (a) M. Fujita, T. Hiyama, *J. Am. Chem. Soc.* 1984, 106, 4629-4630; (b) L. Gan, M. A. Brook, *Can. J. Chem.* 2006, 84, 1416-1425; (c) I. Ojima, M. Nihonyanagi, Y. Nagai, *Bull. Chem. Soc. Jpn.* 1972, 45, 3722-3722; (d) H. Mimoun, J. V. de Saint Laumer, L. Giannini, R. Scopelliti, C. Floriani, *J. Am. Chem. Soc.* 1999, 121, 6158-6166.

[5] (a) S. Bhattacharyya, *J. Org. Chem.* 1998, 63, 7101-7102; (b) T. Mizuta, S. Sakaguchi, Y. Ishii, *J. Org. Chem.* 2005, 70, 2195-2199.

[6] M. P. Doyle, C. T. West, *J. Org. Chem.* 1975, 40, 3835-3838.

[7] (a) V. Gevorgyan, M. Rubin, J.-X. Liu, Y. Yamamoto, *J. Org. Chem.* 2001, 66, 1672-1675; (b) N. Gandhamsetty, J. Jeong, J. Park, S. Park, S. Chang, *J. Org. Chem.* 2015, 80, 7281-7287; (c) S. Rendler, M. Oestreich, *Angew. Chem. Int. Ed.* 2008, 47, 5997-6000; *Angew. Chem.* 2008, 120, 6086-6089.

[8] A. Fedorov, A. Toutov, N. Swisher, R. Grubbs, *Chem. Sci.* 2013, 4, 1640-1645.

[9] (a) M. Rubio, J. Campos, E. Carmona, *Org. Lett.* 2011, 13, 5236-5239; (b) K. Matsubara, T. Iura, T. Maki, H. Nagashima, *J. Org. Chem.* 2002, 67, 4985-4988; (c) S. E. Denmark, J. D. Baird, *Chem. Eur. J.* 2006, 12, 4954-4963; (d) T. T. Metsanen, M. Oestreich, *Organometallics* 2015, 34, 543-546; (e) S. Diez-Gonzaález, N. M. Scott, S. P. Nolan, *Organometallics* 2006, 25, 2355-2358.

[10] (a) H. Zhou, H. Sun, S. Zhang, X. Li, *Organometallics* 2015, 34, 1479-1486; (b) H. Reuther, *Z. Anorg. Allg. Chem.* 1953, 272, 122-125; (c) J. M. Roth, A. M. Brook, H. B. Penny, *J. Organomet. Chem.* 1996, 521, 65-74; (d) S. A. Wells, *Org. Process Res. Dev.* 2010, 14, 484-484; (e) M. Zhao, W. Xie, C. Cui, *Chem. Eur. J.* 2014, 20, 9259-9262; (f) K. Junge, B. Wendt, D. Addis, S. Zhou, S. Das, M. Beller, *Chem. Eur. J.* 2010, 16, 68-73.

[11] K. Revunova, I. G. Nikonov, *Chem. Eur. J.* 2014, 20, 839-845.

[12] M. T. Attar-Bashi, C. Eaborn, J. Vencl, R. D. Walton, *J. Organomet. Chem.* 1976, 117, C87-C89.

[13] (a) J. K. Puri, R. Singh, V. K. Chahal, *Chem. Soc. Rev.* 2011, 40, 1791-1840; (b) C. L. Frye, G. A. Vincent, W. A. Finzel, *J. Am. Chem. Soc.* 1971, 93, 6805-6811; (c) V. Pestunovich, S. Kirpichenko, M. Voronkov, Silatranes. In *The Chemistry of Organic Silicon Compounds*; Z. Rappoport, Y. Apeloig, Wiley, Chishester, U K, 1998, vol. 2, p. 1447-1537; (d) M. G. Voronkov, V. M. Dyakov, S. V. Kirpichenko, *J. Organomet. Chem.* 1982, 233, 1-147; (e) G. J. Verkade, *Acc. Chem. Res.* 1993, 26, 483-489.

[14] (a) M. Kira, K. Sato, H. Sakurai, *J. Org. Chem.* 1987, 52, 948-949; (b) C. Breliere, F. Carre, R. J. P. Corriu, M. Poirier, G. Royo, *Organometallics* 1986, 5, 388-390; (c) M. Deneux, I. C. Akhrem, D. V. Avetisyan, E. I. Mysof, M. E. Vol'pin, *Bull. Soc. Chim. Fr.* 1973, 2638-2642; (d) J. Boyer, C. Breliere, R. J. P. Corriu, A. Kpoton, M. Poirier, G. J. Royo, *J. Organomet. Chem.* 1986, 311, C39-C43.

[15] (a) J. Pietruszka, *Science Synthesis* 2002, 4, 159-185; (b) C. Chuit, R. J. P. Corriu, C. Reye, in: *Chemistry of Hypervalent Compounds*, Wiley-VCH, Weinheim, Germany, 1999, p. 81-146.

[16] (a) J. M. Aizpurua, M. Lecea, C. Palomo, *Can. J. Chem.* 1986, 64, 2342-2347; (b) J. M. Aizpurua, C. Palomo, *Tetrahedron Lett.* 1984, 25, 1103-1104; (c) C. T. West, S. J. Donnelley, D. A. Kooistra, M. P. Doyle, *J. Org. Chem.* 1973, 38, 2675-2681.

[17] The Cannizzaro Reaction. T. A. Geissman, *Org. React.* 2011, 2, 94-113.

[18] (a) S. S. Karlov, *Inorg. Chim. Acta* 2007, 360, 563-578; (b) A. C. Black, *Bioorg. Med. Chem. Lett.* 2002, 12, 3521-3523; (c) E. Lukevics, *Main Group Met. Chem.* 2000, 23, 761-764; (d) V. A. Pestunovich, *Dokl. Akad. Nauk* 1982, 263, 904-906.

[19] G. I. Zelcans, M. G. Voronkov, *Chem. Heterocycl. Compd.* 1967, 3, 296-298.

[20] (a) Magano, J.; Dunetz, J. R. *Org. Process. Res. Dev.* 2012, 16, 1156-1184; (b) Abdel-Magid, A. F., Ed. Reductions in Organic Synthesis. Recent Advances and Practical Applications; ACS Symposium Series; American Chemical Society: Washington, D C, 1998; (c) Hudlicky, M., Ed. Reductions in Organic Chemistry; John Wiley & Sons, Ltd.: Chichester, U.K., 1984; (d) Abdel-Magid, A. F. Reduction of C=O to CHOH by Metal Hydrides. In Comprehensive Organic Synthesis; Knochel, P., Molander, G. A., Eds.; Elsevier: Oxford, 2014; Vol. 8, pp 1-84.

[21] Cho, B. T. *Chem. Soc. Rev.* 2009, 38, 443-452.

[22] Larson, G. L.; Fry, J. L. *Org. React.* 2008, 71, 1-737.

[23] (a) Wang, D.; Chan, T. H. *Tetrahedron Lett.* 1983, 24, 1573-1576; (b) Lipshutz, B. H.; Noson, K.; Chrisman, W.; Lower, A. *J. Am. Chem. Soc.* 2003, 125, 8779-8789; (c) Liu, S.; Peng, J.; Yang, H; Bai, Y.; Li, J.; Lai, G. *Tetrahedron* 2012, 68, 1371-1375.

[24] (a) Hog, D. T.; Oestereich, M. *Eur. J. Org.* 2009, 136, 5047-5056; (b) Chen, J.; Lalancette, R. A.; Jäkle, F.; *Chem. Commun.* 2013, 49, 4893-4895; (c) Metsänen, T. T.; Hrobàrik, P.; Klare, H. F. T.; Kaupp, M.; Oestereich, M. *J. Am. Chem. Soc.* 2014, 136, 6912-6915.

[25] (a) Boyer, J.; Corriu, R. J. P.; Perz, R.; Reye, C. *Tetrahedron* 1981, 37, 2165-2171; (b) Corriu, R. J. P.; Perz, R.; Reye, C. *Tetrahedron* 1983, 39, 999; (c) Kobayashi, Y.; Takahisa, E.; Nakano, M.; Watatani, K. *Tetrahedron* 1997, 53, 1627-1634; (d) Drew, M. D.; Lawrence, N. J.; Watson, W.; Bowles, S. A. *Tetrahedron Lett.* 1997, 38, 5857-5860.

[26] (a) Hosomi, A.; Hayashida, H.; Kohra, S.; Tominaga, Y. *J. Chem. Soc., Chem. Commun.* 1986, 1411; (b) Kohra, S; Hayashida, H.; Tominaga, Y.; Hosomi, A. *Tetrahedron Lett.* 1988, 29, 89; (c) Schiffers, R.; Kagan, H. B. *Synlett.* 1997, 1175-1178; (d) Gan, L; Brook, M. A. *Can. J. Chem.* 2006, 84, 1416-1425; (e) Revunova, K; Nikonov, G. I. *Chem. Eur. J.* 2014, 20, 839-845.

[27] LaRonde, F. J.; Brook, M. A. *Inorg. Chim. Acta* 1999, 296, 208-221.

[28] (a) Corriu, R. J. P. *J. Organomet. Chem.* 1990, 400, 81-106; (b) Rendler, S.; Oestreich, M., Synthesis 2005, 11, 1727; (c) Denmark, S. E.; Beutner, G. L., *Angew. Chem. Int. Ed.* 2008, 1560.

[29] (a) Korlyukov, A. A.; *Russ. Chem. Rev.* 2015, 84, 422-440; (b) Marin-Luna, M.; Alkorta, I.; Elguero, J. *J. Organomet. Chem.* 2015, 794, 206-215.

[30] Frye, C. L.; Vogel, G. E.; Hall, J. A. *J. Am. Chem. Soc.* 1961, 83, 996.

[31] (a) Voronkov, M. G.; Dyakov, V. M.; Kirpichenko, S. V. *J. Organomet. Chem.* 1982, 233, 1-147; (b) Pestunovich, V.; Kirpichenko, S.; Voronkov, M. G. Silatranes and their tricyclic Analogs. In The Chemistry of Organic Silicon Compounds; Rappoport, Z., Apeloig, Y., Eds.; John Wiley & Sons Ltd: Chichester, U.K., 1998; Vol. 2, Chapter 24, pp 1447-1537; (c) Puri, J. K.; Singh, R.; Chahal, V. K. *Chem. Soc. Rev.* 2011, 40, 1791-1840; (c) Singh, G.; Arora, A.;

Mangat, S. S.; Singh, J.; Chaudhary, S.; Kaur, N.; Choquesillo-Lazarte, D. *J. Mol. Struct.* 2015, 1079, 173-181.

[32] Frye, C. L.; Vincent, G. A.; Finzel, W. A. *J. Am. Chem. Soc.* 1971, 93, 6805-6811.

[33] Attar-Bashi, M. T.; Eaborn, C.; Vencl, J.; Walton, D. R. M. *J. Organomet. Chem.* 1976, 117, C87-C89.

[34] Skrypai, V.; Hurley, J. M.; Adler, M. *J. Eur. J. Org. Chem.* 2016, 2207-2211.

[35] Bahia, P. S.; Jones, M. A.; Snaith, J. S. *J. Org. Chem.* 2004, 69, 9289-9291.

[36] Sok, S.; Gordon, M. S. Comp. Theor. Chem. 2012, 987, 2-15.

[37] Corriu, R. J. P. *J. Organomet. Chem.* 1990, 400, 81-106.

[38] Haut, S. A. J. Agric. Food Chem. 1985, 33, 278-280.

[39] Hedin-Dählström, J.; Shrovani, S.; Wikman, S.; Nicholls, I. A. *Tetrahedron: Asymmetry* 2004, 15, 2431-2436.

[40] Dieskau, A. P.; Begouin, J.-M.; Plietker, B. *Eur. J. Org. Chem.* 2011, 5291-5296.

[41] Fujiwara, Y.; Iwasaki, Y.; Maegawa, T.; Monguchi, Y. Sajiki, H. ChemCatChem 2011, 3, 1624-1628.

[42] Mandi, T.; Stephan, D. W. *J. Am. Chem. Soc.* 2014, 136, 15809-15812.

[43] Hegedus, L. S. and Soderberg, B. C. G. *Transition Metals in the Synthesis of Complex Organic Molecules*, 3rd ed. University Science Books: Sausalito, CA, 2010. Chapter 3.

[44] Schiffers, R. and Kagan, H. B. Asymmetric Catalytic Reduction of Ketones with Hypervalent Trialkoxysilanes. *Synlett* 1997(10), 1175-1178.

[45] Voronkov, M. G., D'yakov, V. M., and Kirpichenko, S. V. Silatranes. *Journal of Organometallic Chemistry* 1982, 233, 1-147.

[46] Mun, S-d., Lee J., Kim, S. H., Hong Y., Ko, Y., Shin Y. K., Lim J. H., Hong, C. S., Do, Y. and Kim, Y. Titanatranes containing tetradentate ligands with controlled steric hindrance. *Journal of Organometallic Chemistry* 2007, 692, 3519-3525.

[47] (a) Chang, I.-S. and Willis, C. J. Fluorinated alkoxides. Part XI. Studies on highly fluorinated amino-alcohols and their metal derivatives. *Canadian Journal of Chemistry* 1977, 55, 2465-2472; (b) Shanklin, J. R., Johnson, C. R., Ollinger, J. and Coates, R. M. Conversion of Ketones to Epoxides via β-Hydroxy Sulfides. *Journal of the American Chemical Society* 1973, 95, 3429-3431.

[48] Jones et al., J. Org. Chem., 1991, 763-769.

[49] Corey, E. J.; Helal, C. *J. Angew. Chem., Int. Ed. Engl.* 1998, 37, 1986-2012.

[50] Duran, J.; Brugat, N.; Polo, A.; Segura, C.; Real, J.; Fontrodona, X.; Benet-Buchholz, J. *Organometallics*, 2003, 22, 3432-3438.

[51] Wagner, G.; Herrmann, R.; Pedersen, B.; Scherer, W. Z. Naturforsch. B Chem. Sci., 2001, 56, 25-38.

What is claimed is:

1. A method of producing an alcohol, comprising:
reducing an aldehyde or a ketone with a hydridosilatrane;
wherein the reducing is carried out with an activator, and the activator comprises a strong base.

2. The method of claim 1, wherein the reducing is reducing the ketone.

3. The method of claim 1, wherein the hydridosilatrane comprises 1-hydrosilatrane.

4. The method of claim 1, wherein the reducing is carried out with a solvent, and the solvent is a polar solvent.

5. The method of claim 4, wherein the solvent is water.

6. The method of claim 2, wherein:
the ketone is a prochiral ketone,
the alcohol produced is a chiral alcohol, and
one enantiomer of the chiral alcohol is produced in excess of the other enantiomer.

7. The method of claim 6, wherein the one enantiomer is produced with an ee of at least 60%.

8. The method of claim 6, wherein the activator is a chiral activator.

9. The method of claim 6, wherein the hydridosilatrane is a chiral hydridosilatrane comprising a bulky group.

10. The method of claim 1, wherein the reaction is carried out at a temperature of at most 100° C.

11. The method of claim 4, wherein:
the hydridosilatrane comprises 1-hydrosilatrane,
the activator comprises an alkali hydroxide and/or an alkoxide,
the solvent is selected from the group consisting of dimethylformamide (DMF); tetrahydrofuran (THF); acetonitrile; dichloromethane (DCM); water and alcohols,
the reaction is carried out at a temperature of at most 100° C., and
the alcohol is produced in a yield of at least 90% based on the aldehyde or ketone.

12. A method of producing an alcohol, comprising:
reducing an aldehyde or a ketone with a hydridosilatrane in water,
wherein the reducing is carried out with an activator, and the activator comprises a strong base.

13. The method of claim 12, wherein the hydridosilatrane comprises 1-hydrosilatrane.

14. A method of producing a pharmaceutical compound, comprising:
forming an alcohol by the method of claim 1, and
forming the pharmaceutical compound from the alcohol.

15. A method of producing a pharmaceutical compound, comprising:
forming an alcohol by the method of claim 12, and
forming the pharmaceutical compound from the alcohol.

16. The method of claim 1, wherein the reducing is reducing the aldehyde.

17. The method of claim 1, wherein the activator comprises an alkali hydroxide and/or an alkoxide.

18. The method of claim 4, wherein the solvent is selected from the group consisting of dimethylformamide (DMF); tetrahydrofuran (THF); acetonitrile; dichloromethane (DCM); and alcohols.

19. The method of claim 1, wherein the alcohol is produced in a yield of at least 75% based on the aldehyde or ketone.

20. The method of claim 8, wherein the chiral activator is an amino alkoxide.

21. The method of claim 1, wherein the alcohol is produced in a yield of at least 75% based on the aldehyde or ketone.

22. The method of claim 12, wherein the reducing is reducing the aldehyde.

23. The method of claim 12, wherein the reducing is reducing the ketone.

24. The method of claim 23, wherein:
the ketone is a prochiral ketone,
the alcohol produced is a chiral alcohol, and
one enantiomer of the chiral alcohol is produced in excess of the other enantiomer.

25. The method of claim 6, wherein the activator is a chiral activator.

\* \* \* \* \*